United States Patent
Dor Zidon

(10) Patent No.: US 11,529,475 B2
(45) Date of Patent: Dec. 20, 2022

(54) INSUFFLATION APPARATUS AND METHODS AND A GAS GENERATING CARTRIDGE THEREFOR

(71) Applicants: Shahar Dor Zidon, Auckland (NZ); Fisher & Paykel Healthcare Limited, Auckland (NZ)

(72) Inventor: Shahar Dor Zidon, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 948 days.

(21) Appl. No.: 14/760,959

(22) PCT Filed: Jan. 10, 2014

(86) PCT No.: PCT/NZ2014/000005
§ 371 (c)(1),
(2) Date: Dec. 16, 2015

(87) PCT Pub. No.: WO2014/112886
PCT Pub. Date: Jul. 24, 2014

(65) Prior Publication Data
US 2015/0367087 A1 Dec. 24, 2015

Related U.S. Application Data

(60) Provisional application No. 61/752,843, filed on Jan. 15, 2013.

(51) Int. Cl.
*A61M 13/00* (2006.01)
*A61M 16/10* (2006.01)
(Continued)

(52) U.S. Cl.
CPC .............. *A61M 13/003* (2013.01); *B01J 7/00* (2013.01); *A61M 13/006* (2014.02);
(Continued)

(58) Field of Classification Search
CPC .. A61M 13/00; A61M 13/003; A61M 13/006; A61M 16/16;
(Continued)

(56) References Cited

U.S. PATENT DOCUMENTS 4,585,624 A * 4/1986 Young ................. B01J 7/00
101/415.1
4,735,603 A 4/1988 Goodson et al.
(Continued)

FOREIGN PATENT DOCUMENTS

JP 2002/053315 A 2/2002
JP 2010/188329 A 9/2010
(Continued)

OTHER PUBLICATIONS

Machine Translation of JP 2010/188329 A from https://www4.j-platpat.inpit.go.jp/cgi-bin/tran_web_cgi_ejje?u=http://www4.j-platpat.inpit.go.jp/eng/translation/201809240916571008532361036652369 14387D3253AF6DDF6F6ED7B479749F6A. Accessed Sep. 23, 2018. 14 Pages.*

(Continued)

*Primary Examiner* — Lauren P Farrar
*Assistant Examiner* — Hamza A Darb
(74) *Attorney, Agent, or Firm* — Knobbe, Martens, Olson & Bear, LLP

(57) ABSTRACT

The invention provides an insufflation apparatus having a housing and a gas generator arranged to be, at least partially, mounted to the housing. The housing includes a gas outlet for delivering gas to a patient and a gas storage chamber arranged to store gas and deliver it to the gas outlet. The gas generator includes a cartridge mount on the housing adapted to receive a gas generating cartridge, the gas generating cartridge containing gas generating material that generates gas that is delivered to the gas storage chamber. The (Continued)

invention also provides alternative insufflation apparatus, a gas cartridge and a method of generating insufflation gas.

26 Claims, 10 Drawing Sheets

(51) Int. Cl.
 *A61M 16/16* (2006.01)
 *B01J 7/00* (2006.01)
(52) U.S. Cl.
 CPC .......... *A61M 16/101* (2014.02); *A61M 16/16* (2013.01); *A61M 2202/0225* (2013.01); *A61M 2205/18* (2013.01); *A61M 2205/3337* (2013.01); *A61M 2205/3653* (2013.01); *A61M 2205/505* (2013.01); *A61M 2205/75* (2013.01); *A61M 2205/8206* (2013.01); *A61M 2205/8231* (2013.01); *A61M 2205/8237* (2013.01); *A61M 2206/14* (2013.01)
(58) Field of Classification Search
 CPC .......... A61M 2202/02–0291; A61M 2205/8218–8231; A61M 16/009; A61M 16/042; A61M 2016/0413; A61M 2016/103; A61M 16/101; A61M 2202/0225; A61M 2205/18; A61M 2205/3337; A61M 2205/3653; A61M 2205/505; A61M 2205/75; A61M 2205/8206; A61M 2205/8237; A61M 2206/14; B01J 7/00; B01J 19/14; B01J 7/02; C01B 32/50
 See application file for complete search history.

(56) References Cited

U.S. PATENT DOCUMENTS

| | | | | |
|---|---|---|---|---|
| 5,514,087 | A * | 5/1996 | Jones | A61M 13/003 604/26 |
| 8,118,769 | B2 * | 2/2012 | Diemunsch | A61M 11/041 604/25 |
| 8,168,048 | B1 | 5/2012 | Maget | |
| 9,095,669 | B2 * | 8/2015 | Costovici | A61M 13/003 |
| 2003/0236015 | A1 * | 12/2003 | Edirisuriya | A61M 16/08 439/191 |
| 2004/0023087 | A1 * | 2/2004 | Redmond | C01B 3/0031 429/515 |
| 2004/0194439 | A1 * | 10/2004 | Tang | B01D 46/2403 55/484 |
| 2009/0250054 | A1 * | 10/2009 | Loncar | A61M 16/0093 128/203.14 |
| 2010/0242961 | A1 * | 9/2010 | Mougel | A61M 16/1055 128/203.16 |
| 2012/0164056 | A1 | 6/2012 | Haddad et al. | |

FOREIGN PATENT DOCUMENTS

| | | | | |
|---|---|---|---|---|
| JP | | 2010188329 A | * 9/2010 | |
| JP | | 2010188329 A | * 9/2010 | |
| WO | WO-2012131120 A1 | * 10/2012 | .......... A61M 13/003 |
| WO | WO 2013/008070 A1 | 1/2013 | |

OTHER PUBLICATIONS

Machine Translation of JP 2010/188329 A from https://www4.j-platpat.inpit.go.jp/cgi-bin/tran_web_cgi_ejje?u=http://www4.j-platpat.inpit.go.jp/eng/translation/201809240916571008532361036652369 14387D3253AF6DDF6F6ED7B479749F6A. Accessed Sep. 23, 2018. 14 Pages. (Year: 2018).*
Machine Translation of JP 2010/188329 A from https://www4.j-platpat.inpit.go.jp/cgi-bin/tran_web_cgi_ejje?u=http://www4.j-platpat.inpit.go.jp/eng/translation/201809240916571008532361036652369 14387D3253AF6DDF6F6ED7B479749F6A. Accessed Sep. 23, 2018. 14 Pages. (Year: 2018) (Year: 2018).*
"Apex" Dictionary.com. https://www.dictionary.com/browse/apex?s=t. Accessed Jan. 16, 2020. (Year: 2020).*
International Search Report; PCT/NZ2014/000005; dated May 2, 2014; 5 pages.

* cited by examiner

INSUFFLATION APPARATUS AND METHODS AND A GAS GENERATING CARTRIDGE THEREFOR

BACKGROUND OF THE INVENTION

Field of the Invention

This invention relates to insufflation apparatus and methods, as well as a gas generating cartridge therefor.

Description of the Related Art

It is known to provide an insufflation apparatus comprising an insufflator arranged to deliver gas to a body cavity of a patient to inflate the body cavity, or to at least resist collapse of the body cavity during a medical procedure. Examples of such a medical procedure are laparoscopic and endoscopic procedures, although an insufflator may be used with any other type of medical procedure as required. Insufflation apparatus may also be used for "open" surgical procedures. For example, an insufflator may be used to fill the cavity with excess gas spilling outward from the opening or may be used to provide a layer of gas over exposed internal body parts where there is no discernible cavity. For these procedures, rather than serving to inflate a cavity, the gas can be used to prevent or reduce desiccation and infection by covering exposed internal body parts with a layer of heated, humidified, sterile gas. Throughout the specification, references to "insufflation" include all such applications including both keyhole and more open procedures.

Endoscopic procedures enable a body cavity to be visualized by inserting an endoscope or the like through natural openings or small punctures to generate an image of the body cavity. Laparoscopy procedures typically insert a surgical instrument through natural openings or small punctures to perform a surgical procedure in the body cavity. In some cases an initial endoscopic procedure may be carried out to assess the body cavity, and then a subsequent laparoscopy carried out to operate on the body cavity. Such procedures are widely used such as for example on the peritoneal cavity, or during a thoracoscopy, colonoscopy, gastroscopy or bronchoscopy.

It is desirable to be able to inflate, or maintain, the body cavity by using an insufflator which delivers gas, usually carbon dioxide, into the body cavity. An insufflator typically comprises an adjustable throttling pressure regulator and a gas flow controller. The insufflator is connected to a remote source of pressurized gas, and is operative to control the pressure of the gas from the remote source to a level suitable for pumping into the body cavity, usually via a cannula or needle connected to the apparatus and inserted into the body cavity.

It has been proposed to provide an insufflation system which includes a gas temperature controller, and/or a moisture controller. The internal body temperature is typically around 37° C. and it can be desirable to closely match the temperature of the gas delivered from the insufflator to the normal body temperature. Likewise, the gas delivered may be relatively dry which can cause damage to the body cavity including cell death and adhesions for example. The moisture controller may therefore comprise a humidifier located in the gas flow path to deliver water vapour to the gas stream prior to entering the body cavity.

U.S. Pat. No. 8,206,337 of Fisher & Paykel Healthcare Limited discloses an insufflation apparatus comprising an insufflator arranged to be connected to a remote source of pressurized gas, as may be provided via a gas supply system in a hospital for example. The insufflator delivers gas, via tubing, to a humidifier comprising a receptacle of fluid and a fluid heater to heat the fluid and generate fluid vapour. The humidified gas is delivered to the patient via further tubing which may also be heated. In one example, the above components are located in separate housings connected together via suitable tubing and/or electrical connections. In another example, the insufflator and humidifier are located in a common housing but this still needs to be connected to a remote gas supply via suitable tubing. Therefore, whilst the apparatus assists in controlling the temperature and humidity of the gas delivered to the patient, a remote source of pressurized gas is still required.

An insufflation apparatus is typically used by medical personnel in a hospital or the like, or in an ambulance. It may also be used in the field, for example, in a combat zone, or temporary medical centre. Prior art apparatus all require connection to a suitable remote source of pressurized gas. This therefore requires both such a gas source, and that the apparatus is in relatively close proximity to that gas source. This limits the scope and ease of use of an insufflation apparatus. Additionally, the connection, via suitable pipework or the like, can be unwieldy and can represent a hazard in an emergency situation in that the pipework may be accidentally knocked, or disconnected, during use. It can sometimes be required to transfer a patient from one location to another. Even when in the same building, the requirement for a physical connection to a remote source of gas makes this difficult.

OBJECT OF THE INVENTION

It is therefore an object of the invention to provide an insufflation apparatus which overcomes or at least ameliorates one or more of the disadvantages of the prior art, or alternatively at least provides the public or industry with a useful choice.

Further objects of the invention will become apparent from the following description.

SUMMARY OF THE INVENTION

Accordingly in a first aspect, the invention may broadly be said to consist in an insufflation apparatus comprising a housing and a gas generator arranged to be, at least partially, mounted on or in the housing. The housing comprises a gas outlet for delivering gas to a patient and a gas storage chamber arranged to store gas and to deliver gas to the gas outlet. The gas generator comprises a cartridge mount on the housing adapted to receive a gas generating cartridge, the gas generating cartridge containing and/or configured to receive gas generating material. The cartridge, cartridge mount and gas storage chamber are arranged so that, in use, when the apparatus is in an active mode, the cartridge is in fluid communication with the gas storage chamber when the cartridge is mounted on the cartridge mount, and gas is generated from the gas generating material in the cartridge and delivered to the gas storage chamber.

Preferably the apparatus comprises the cartridge.

Preferably the cartridge is removable. Locking means may be provided to prevent accidental removal and/or to hold the cartridge in place against the pressure generated by the chemical reaction.

The active mode may initiate automatically upon mounting of the cartridge on the cartridge mount. In another example, the active mode may be selectively initiated.

A controller may be provided to control the operation of the apparatus. The controller may be operative to control initiation and termination of the active mode. The controller may be arranged to control the other primary functions of the apparatus. The controller may comprise a user interface provided on the housing. The user interface may incorporate a graphic display, which may be a touchscreen display for example.

Preferably a closure is provided at the cartridge and is arranged to seal the gas generating material in the cartridge, the apparatus being arranged to at least partially open the closure when the apparatus is in the active mode. Opening of the closure may initiate gas generation.

The closure may comprise a region of predetermined weakness, the apparatus comprising a perforator arranged to perforate the region of predetermined weakness when the apparatus is in the active mode to open the closure, providing for said fluid communication and enabling generated gas to be delivered to the gas storage chamber.

The perforator may be arranged to automatically perforate the region of predetermined weakness when the cartridge is mounted on the cartridge mount, for example, as the cartridge is pressed fully onto the cartridge mount. In another example, the perforator may be selectively controllable to perforate the region of predetermined weakness at a predetermined, or operator selected, time.

As an alternative to the perforator, the apparatus may be configured to generate a pressure differential across the closure that is sufficient to rupture or move the closure to provide the opening. For example, a reaction may be triggered in the gas generating cartridge that releases gas to generate a high pressure inside the gas generating cartridge. Additionally or alternatively, a compressor provided downstream of the gas generating cartridge may create a region of reduced pressure outside of the cartridge.

The closure may comprise a movable barrier, cap or valve arranged to be movable between a closed position, and an open position. The movable barrier, cap or valve may be moved to the open position on mounting of the cartridge, or opened subsequently in response to operator input or control signals of the controller. The generation of pressure differentials across the disclosure may again be used to provide the opening.

Further, a combination of closures may be provided. For example, a thin film or sheet of material may close off an opening of the container with a movable barrier, cap or value positioned inside thereof.

Yet further, at least a portion of the closure may be removable by an operator prior to mounting of the cartridge.

The cartridge mount preferably comprises a cavity in the housing, the cavity being provided with an opening at the exterior of the housing, the cartridge being inserted through the opening and into the cavity, in use.

The cartridge and cartridge mount may comprise respective locking formations arranged to engage to lock the cartridge on the cartridge mount. The locking formations may comprise a snap-fit type formation, or a spring clip, for example, and are preferably configured to enable intentional release of the cartridge from the mount i.e., the locking formations are preferably releasable and lockable. Due to increased pressures generated during generation of gas, the locking formations should hold the cartridge to the mount with sufficient force to exceed that generated by the increased pressures.

The cartridge mount cavity may be defined between at least two opposed walls, the cartridge being received between, and located against, the opposed walls to fix the orientation of the cartridge relative to the cartridge mount. In one example, the cavity may be oblong. In one example, the cavity may comprise a first pair of opposed walls, being side walls, and a second pair of opposed walls, being upper and lower walls. The cavity and cartridge may be configured such that it can be mounted in only one way. For example, a groove in the cartridge may slidably engage a slot of the cavity as it is mounted (or vice versa).

The cartridge mount may comprise a manifold which forms a gas flow path between the cartridge and the gas storage chamber, the manifold being intermediate the cartridge and the gas storage container when the cartridge is mounted on the cartridge mount. The manifold may be arranged to mix gas flowing through the manifold. The manifold may be provided with a gas flow path arranged to encourage mixing of the gas.

In another example, the cartridge mount is arranged such that the cartridge, when mounted on the cartridge mount, forms a fluid connection directly with the gas storage container.

The cartridge mount and the gas storage chamber may be provided with an isolator arranged to isolate the gas storage chamber from the cartridge such that the cartridge can be removed from the cartridge mount without affecting the flow of gas from the gas storage chamber to the gas outlet. Thus once all generated gas has been discharged from the cartridge into the gas storage chamber, the cartridge may be removed and the gas stored in the gas storage chamber subsequently discharged through the outlet at a selected time. Alternatively, it is envisaged that the cartridge could be removed part way through gas generation. Removal of the cartridge may automatically close the closure to terminate gas generation, or at least prevent release of gas from the cartridge.

The gas generating material in the cartridge may be arranged to begin generating gas on exposure to ambient air when the closure is open or partially open. The gas generating material in the cartridge may be arranged to begin generating gas on exposure to other gas generating material in the cartridge. A heater may be provided to, to some extent, control the reaction rate of the gas generating material and thus the rate at which gas is generated. For example, for some embodiments, heating to increase the temperature increases the reaction rate. Heaters may also be provided to ensure that the gas is delivered at the desired temperature. Such heaters may be provided in thermal communication with gas inside the cartridge, the manifold or the gas storage chamber, or elsewhere along the gas path.

In one example, a chamber heater is provided to heat the gas storage chamber. The chamber heater may be controlled via the controller to vary the heat generated in dependence upon the availability of gas from the cartridge. The controller may be arranged to automatically control the chamber heater, or may be arranged to enable the user to selectively control the chamber heater. The chamber heater may comprise a heater coil disposed on at least one of the interior or exterior wall of the gas chamber. Alternatively, the chamber heater may comprise a heater plate adjacent the gas chamber. The chamber heater may be powered from an internal power source located in the housing, such as a battery for example. The battery may be rechargeable and a suitable AC/DC converter may also be provided in the housing in that instance.

The gas chamber may comprise thermal insulation, as may any other element of the apparatus used to store and/or transport gas to a patient.

A gas flow control valve may be provided between the gas chamber and the gas outlet to control the flow of gas through the gas outlet. The gas flow control valve may be controlled automatically or manually, via the controller, to vary at least one of the gas flow rate and the gas pressure. The gas flow control valve may additionally function as a pressure relief valve arranged to vent gas if a predetermined gas pressure is exceeded.

A passive mixing device may be provided in the gas flow path arranged to generate turbulent flow in the gas to mix the constituents of the gas.

A humidifier may be provided in the gas flow path arranged to humidify the gas prior to the gas being delivered to the gas outlet. The humidifier may be controlled by the controller. The controller may be operative to control the humidifier automatically, that is, without operator intervention, to ensure gas is delivered to the outlet having a predetermined humidity. Alternatively or additionally, the controller may be operative to control the humidifier selectively such that the operator can vary the humidity of the gas delivered to the outlet, as required.

The humidifier may comprise an active humidifier comprising a fluid receptacle and a receptacle heater arranged to heat fluid in the fluid receptacle. The fluid receptacle may be removably mounted on the housing, such that the receptacle can be removed and refilled for example. The humidifier may alternatively be a passive humidifier comprising a heat and moisture exchanger arranged to transfer moisture from the ambient air to the gas. The humidifier may be integrated into the gas storage chamber.

A condenser may be provided in the gas flow path. The condenser may be used where a lower level of humidity is desired in the generated gas (i.e., to remove some of the moisture content), particularly if the humidifier is preset to aim for 100% of the relative humidity. A condenser may additionally or alternatively be used to reduce the humidity of the gas prior to storage thereof in the storage chamber. It will be appreciated that since preferred embodiments involve generation of gas in water or an aqueous solution, the gas may have a high humidity and it may be preferable for some applications to reduce that humidity.

An evaporator may be provided in the gas flow path. The evaporator may be used to ensure that any moisture in the gas delivered to the gas outlet is in vapour form.

The invention is not limited to introducing humidity through water. Other liquids or additives may be used in addition to or as an alternative to water.

A flow enhancer may be provided in the gas flow path to provide additional gas flow to the gas outlet. The flow enhancer may comprise a compressor or a blower arranged to blow the gas through the gas flow path, or may comprise an additional source of gas for example. The additional source of gas may be internal of the housing, or may comprise a remote source of gas arranged to be connected to the housing. The flow enhancer can also be used to control the pressure in the cartridge or to compress the gas into the gas storage chamber. According to particular embodiments, reducing the pressure in the cartridge can also be useful to assist in evaporating liquid in the cartridge to increase humidity of the gas or to assist in opening the cartridge.

One or more additional inlets may be provided along the gas flow path to enable additives to be inserted into the gas stream.

Preferably the apparatus is portable. More preferably, the apparatus is portable even when a cartridge is mounted thereon.

By providing all or substantially all elements of the insufflation apparatus in a single housing (albeit the cartridge may be removable), portability of the apparatus is improved, as is the general appearance thereof. Further, since external interconnecting tubes are not required (or at least fewer are required), there is less obstruction or potential hazards posed by the apparatus.

According to a second aspect, the invention may broadly be said to consist in a gas generating cartridge for mounting on a cartridge mount of an insufflation apparatus. The cartridge contains gas generating material and comprises an outlet adapted to form a fluid connection with the insufflation apparatus when the cartridge is mounted on the cartridge mount.

Preferably, the cartridge comprises a closure provided to close the outlet and seal the gas generating material in the cartridge.

Preferably, the closure is adapted to be at least partially opened in use such that the gas generating material reacts to generate gas which flows from the cartridge via the outlet. Alternatively, the opening may be configured to fluidly connect to a separate reaction chamber, wherein opening of the cartridge enables at least a portion of the contents to enter the chamber, the gas then being generated inside the chamber. Such an arrangement may also be incorporated in the insufflation apparatus of the first aspect.

Preferably, the closure is adapted to at least partially open when the cartridge is mounted on or to the insufflation apparatus.

Preferably the cartridge contains at least one material to be used in a reaction for gas generation. More preferably the cartridge contains two or more materials. In one example the cartridge contains at least one solid material and at least one liquid material. In one example, the materials comprise aluminium carbonate and water.

The cartridge may be arranged such that gas is generated when the material in the cartridge is exposed to ambient air. Alternatively, when more than one material is provided, gas may be generated when the materials are exposed to each other.

The cartridge is preferably adapted to generate carbon dioxide.

The closure may comprise one or more of: a movable barrier, movably or removably mounted on the connection; a seal; a wall between the two or more materials contained in the cartridge; and a valve.

The closure may be arranged to be pierced to open the closure such that the gas generating material reacts to generate gas. The closure may comprise a region of predetermined weakness arranged to be pierced. The closure may in this example be single use.

The closure may be arranged to be moved or elastically deformed to open the closure such that the gas generating material reacts to generate gas. The closure may in this example be multiple use, in that the closure can be reused such that the cartridge can be refilled with fresh gas generating material. Such refilling may be achieved via the outlet or via a separate inlet to the cartridge. Alternatively, some other portion of the cartridge may be arranged to be removed or disassembled to allow access to the interior thereof to remove any residual material and/or to insert fresh gas generating material.

The opening and/or closing of the closure may be arranged to be controlled by a controller.

The cartridge may be arranged such that the rate of gas generation is controlled and/or is adjustable using the closure, that is, in dependence upon the degree to which the closure is opened. Thus by opening the closure a relatively small amount, the materials have relatively low exposure and the resulting rate of gas generation is proportionally relatively low. Alternatively, by opening the closure a relatively large amount, the materials have relatively high exposure and the resulting rate of gas generation is proportionally relatively high.

While the cartridge may be reusable/refillable as mentioned above, it may also be disposable (i.e., configured for single use or use until such time as the gas generating material is depleted).

The cartridge may be arranged to be heated to vary the rate of gas generation. In one example, the cartridge may be provided with a cartridge heater. In another example, the cartridge heater may be provided on the cartridge mount.

Preferably the cartridge is adapted to mount on or to the apparatus of the first aspect.

According to a third aspect, there is provided an insufflation apparatus comprising a gas generator configured to generate gas for use in a surgical procedure.

Preferably, the insufflation apparatus comprises a housing and the gas generator is arranged to be, at least partially, mounted or provided on or in the housing, the insufflation apparatus comprising a gas outlet for delivering gas to a patient.

Preferably, the gas generator comprises or defines a reaction chamber.

Preferably, the insufflation apparatus further comprises an activator for activating a reaction inside the reaction chamber in use to generate the gas.

According to one embodiment, the apparatus is configured to bring a first reactant into contact with a second reactant inside the reaction chamber to facilitate or initiate the reaction. For example, the reaction chamber may contain the first reactant and the activator may introduce the second reactant into the reaction chamber and/or move one or other or both of the reactants within the reaction chamber to bring the reactants into contact with one another. Alternatively, the reaction chamber may contain the second reactant and the activator may introduce the first reactant into the reaction chamber.

While description herein generally refers to two reactants being used to generate the gas, the invention is not limited thereto. A single reactant or additional reactants may be used, as required or preferred.

The first reactant may comprise a carbonate material such as aluminium bicarbonate or sodium bicarbonate, and the second reactant may comprise water and/or an acid (or vice versa). As will be appreciated, such an arrangement will produce carbon dioxide gas. Other reactants may be used to produce carbon dioxide or to produce other gases although some adaptation of the apparatus may be required depending on the type of reaction.

According to one embodiment, the first reactant may be substantially solid, defining at least one body. For example, the first reactant may be in the form of one or more elongate bodies or rods. The surface of the body may be contoured to increase the surface area of the body and therefore potentially increase the rate of reaction when brought into contact with the second reactant.

Additionally or alternatively, at least a portion of the first reactant may be provided in powdered or particulate form, or at least comprise one or more smaller bodies. Providing at least a portion of the first reactant in this manner increases the surface area of the first reactant that may be brought into contact with the second reactant, again potentially increasing the rate of reaction. This may be of particular benefit during the early stages of the reaction in facilitating sufficient generation of gas in a shorter amount of time than would otherwise be achievable.

The apparatus may comprise one or more heaters to heat the contents of the reaction chamber and/or to heat the first reactant and/or the second reactant before it is or they are provided in the reaction chamber. The controlled provision of heat may be used to control the rate of the reaction to some extent, at least for some embodiments, particularly to accelerate the rate of reaction by providing additional heat.

The heaters may comprise one or more heater elements provided within the reaction chamber and/or within the wall of the reaction chamber and/or otherwise in thermal communication with the reaction chamber. For example, a heater coil may at least partially circumscribe the reaction chamber. Where a reactant is provided in solid form, said reactant may be provided or coated on a heater element, similar to an immersion heater element.

The reaction chamber may comprise a plurality of sub-chambers, in which case the activator may be configured to bring the reactants into contact within any one or more of said sub-chambers. As will be appreciated, using a larger number of similarly configured sub-chambers will increase the reaction rate within the reaction chamber. The sub-chambers may be formed by partitioning walls within the reaction chamber that divide the reaction chamber into a plurality of smaller reaction chambers.

Further, the activator may be configured to vary the sub-chambers that are in use, i.e., those that are generating gas, at a particular time. The rate of gas generation can thus be controlled by controlling the quantity of sub-chambers that are in operation at the same time.

According to one embodiment, the sub-chambers each comprise the first reactant and are selectively in fluid communication with the second reactant. The second reactant may be held in a reservoir within the reaction chamber or within the housing or external thereto. Further, each sub-chamber is in fluid communication with the outlet to enable the generated gas to be delivered to a patient, including via external peripheral equipment and other intermediate processors, as will become more apparent herein below.

According to a presently preferred embodiment, the sub-chambers are provided in the reaction chamber and elevated above the base thereof or of the housing. At least one aperture is provided in the base of each chamber to allow the second reactant present in the space below the sub-chambers to enter therethrough. Valve means may be provided about each aperture, selectively controlling whether the apertures are open or closed. Alternatively, a moveable blocking member may be provided that fluidly isolates at least a portion of the space below the sub-chambers, thereby preventing the second reactant entering into at least one of the sub-chambers. Movement of the blocking member can be used to increase or decrease the number of sub-chambers in fluid communication with the reservoir.

Preferably, the reaction chamber is provided in the form of a removable cartridge so as to enable a replacement cartridge to be provided when the reactants have been depleted. Additionally or alternatively, only a portion of the reaction chamber may be removable. For example, the sub-chambers or a subset thereof may be removable. Additionally or alternatively, the reaction chamber may comprise a plurality of removable cartridges, enabling one or more cartridges to be replaced while one or more other cartridges are used to generate gas. Additionally or alternatively, one or more sealably closeable ports may be provided in the reaction chamber to enable one or more reactants to be fed therethrough so as to replenish the reaction chamber with at least one of the reactants.

Preferably, the cartridge is of a form similar to that envisaged in the first and second aspects, and reference is made to these aspects for further description of the cartridge design and its coupling to the wider apparatus. In addition, it will be appreciated that the cartridge embodiments described as part of this third aspect (above and below) are also applicable to the cartridges envisaged in the first and second aspects.

As with the insufflation apparatus of the first aspect, additional processors of the gas may be provided. For example, a gas storage chamber may be provided to store the generated gas prior to being delivered to a patient. Further, processors may condition the gas such as by humidifying or dehumidifying the gas or heating or cooling the gas. Additives may also be introduced into the gas.

Processors such as a blower and/or profiled passageways may be used to control the pressure and/or flow rate of the gas delivered to the patient.

Again, reference is made to the first and second aspects, as well as the description below for further description of the processors, and the control thereof.

According to another embodiment, there is provided an insufflation apparatus comprising a housing and a gas generator arranged to be, at least partially, mounted or provided on or in the housing. The housing comprises a gas outlet for delivering gas to a patient. The gas generator comprises or defines a reaction chamber that contains or is configured to receive a reactant. The insufflation apparatus further comprises an activator for activating a reaction inside the reaction chamber in use to generate the gas, and the activator comprises one or more electrodes, whereby charge applied to the one or more electrodes, in use, activates the reaction to generate the gas.

According to a preferred embodiment, the reactant comprises a positively charged, carbon dioxide loaded amines solution (e.g. Piperazine or Diethanolamine), such that when one or more of the electrodes is negatively charged, the carbon dioxide loaded amines solution decomposes to release carbon dioxide. Preferably, the one or more electrodes comprises a copper core.

Switching circuitry may be provided to selectively apply charge to the one or more electrodes or to a subset thereof. Alternatively, according to a presently preferred embodiment, the one or more electrodes extend into the reaction chamber and are provided with an electrical coupling external thereto. For example, the one or more electrodes may extend out of the reaction chamber or have their ends exposed via corresponding aperture(s) in a wall of the reaction chamber, or additional means for electrical coupling may be provided as would be apparent to those skilled in the art based on the disclosure herein. According to this embodiment, the activator may comprise a moveable block that applies negative charge to one or more of the electrodes as it is brought into contact therewith.

Again, other features of this embodiment, including the control thereof, may be drawn from the first and second aspects as well as the prior discussion with regards the third aspect and the subsequent description. For example, at least a portion of the apparatus may comprise or be configured as a removable cartridge to facilitate replenishment of the reactant. Further, processors may be provided to condition the generated gas and/or the contents of the reaction chamber. Further, the arrangement may be adapted to generate different gases and/or to generate carbon dioxide using a different reactant and/or electrode material.

According to another embodiment, there is provided an insufflation apparatus comprising a housing and a gas generator arranged to be, at least partially, mounted or provided on or in the housing. The housing comprises a gas outlet for delivering gas to a patient. The gas generator comprises or defines a reaction chamber. The insufflation apparatus further comprises an activator for activating gas generation inside the reaction chamber in use to generate the gas. The reaction chamber contains or is configured to receive an absorber/desorber and the activator is configured to generate the gas by activating desorption of the gas from the absorber/desorber.

Preferably, the reaction chamber is at least partially filled or configured to be filled with a medium such as water or an aqueous solution, wherein the absorber/desorber is at least partially submersed in the medium. Other media may alternatively be used, depending at least in part on the gas to be generated and/or properties of the absorber/desorber.

Preferably, the absorber/desorber comprises one or more microporous metal organic frameworks, although other absorbers/desorbers may be used as will be apparent to those skilled in the art, and may be adapted depending on the gas to be generated. Where a metal organic framework is used, preferably it comprises mmen-Mg2 or Cu-BTC.

Preferably, the apparatus comprises one or more heaters to heat at least a portion of the contents of the reaction chamber. The controlled provision of heat can be used to control the rate of release of the gas from the absorber/desorber, at least to some extent. Preferably, the one or more heaters are configured to heat at least a portion of the reaction chamber contents to a temperature of between 50° C. and 100° C.

The one or more heaters may comprise one or more heater elements provided within the reaction chamber and/or within a wall of the reaction chamber and/or otherwise in thermal communication with the reaction chamber. For example, a heater coil may at least partially circumscribe the reaction chamber.

The reaction chamber may comprise a plurality of sub-chambers, in which case, the one or more heater elements may be configured to heat the contents of any one or more selected sub-chambers. Thus a single or a higher number of sub-chambers may be used depending on the required rate of gas generation. Additionally or alternatively, when one or more sub-chambers are depleted (i.e., the absorber/desorber has desorbed substantially all of the gas absorbed thereby or the rate of release of the gas becomes insufficiently low), the activator may control the apparatus such that a different one or more sub-chambers are then used either in addition or isolation from the previous one or more sub-chambers that were used. Control of switching in this manner may be determined based on empirical data generated by testing of the apparatus and/or by using sensors to monitor characteristics of the generated gas.

Switching circuitry may be provided to selectively apply charge to the one or more heater elements. Alternatively, according to a presently preferred embodiment, the one or more heater elements may be configured similar to the abovementioned one or more electrodes such that they extend into the reaction chamber and are provided with an electrical coupling external thereto. For example, the one or more heater elements may extend out of the reaction chamber or have their ends exposed via corresponding aperture(s) in a wall of the reaction chamber or additional means for electrical coupling may be provided as would be apparent to those skilled in the art based on the disclosure herein. According to this presently preferred embodiment, the activator may comprise a moveable block that electrically couples the one or more heater elements to a power supply when the block is brought into physical contact therewith.

Again, other features of this embodiment, including the control thereof, may be drawn from the first and second aspects as well as the prior discussion with regards the third aspect and the subsequent description. For example, at least a portion of the apparatus may comprise or be configured as a removable cartridge to facilitate replenishment of the gas generating material. For example, at least the absorber/desorber may be removable to facilitate reabsorption with the gas. Additionally or alternatively, at least a portion of the reaction chamber may be removable. For example, the complete reaction chamber and/or one or more sub-chambers thereof may be removable. Additionally or alternatively, one or more ports may be provided to replenish the reaction chamber with gas generating material. Further, one or more processors may be provided to condition the generated gas. Further, the arrangement may be adapted to generate different gases or to generate carbon dioxide using a different absorber/desorber and/or medium.

According to a fourth aspect of the invention there is provided an insufflation apparatus comprising a gas inlet in fluid communication with a gas outlet for delivering gas to a patient. A first heater is provided between the gas inlet and the gas outlet and is arranged to control the pressure of the gas delivered to the patient. A second heater is provided between the gas inlet and the gas outlet and is arranged to control the temperature of the gas delivered to the patient. Other features of this aspect may be drawn from the first, second and third aspects.

According to a fifth aspect there is provided a method of generating insufflation gas, the method comprising: providing an insufflation apparatus according to the first aspect or the third aspect or the fourth aspect; and/or providing a gas generating cartridge according to the second aspect; and/or mounting a gas generator on or to an insufflation apparatus and/or mounting a gas generating cartridge on or to an insufflation apparatus.

Preferably the method comprises at least partially opening an outlet of the cartridge to enable gas to flow from the cartridge to the insufflation apparatus. Alternatively, opening of the outlet may enable a reactant to flow from the cartridge to be received in a separate reaction chamber.

Preferably the method comprises controlling any one or more of: the degree that the outlet is open; a temperature of the cartridge; a temperature of the generated gas; a humidity of the generated gas; a flow speed of the generated gas; a pressure of the gas; and/or a rate of gas generation.

Preferably, the method comprises removing the cartridge from the insufflation apparatus, preferably when said gas generating material is depleted, at least to a level whereby useful gas generation is not attainable.

Preferably, the method comprises mounting a replacement cartridge.

The method may comprise refilling a used cartridge with fresh gas generating material. This may be performed with the cartridge detached or attached to the insufflation apparatus. Additionally or alternatively, the method may comprise reconditioning a used cartridge such that it may be re-used. Some embodiments provide for reconditioning or replenishing of a cartridge, at least in part, using one or more by-products of the method and/or gas recycled back to the apparatus after use in a surgical procedure.

According to a sixth aspect, there is provided a method of generating insufflation gas, the method comprising: providing a gas generator comprising a reaction chamber containing or configured to contain gas generating material, and providing an activator for activating the generation of gas within the reaction chamber.

Further features of this method are analogous to features described hereinabove and below, including those described with reference to insufflation apparatus. Further, the generation of gas may be performed by a desorption process.

According to a seventh aspect, there is provided a method of generating insufflation gas, the method comprising activating gas generation within a reaction chamber.

Preferably, the method comprises initiating and/or controlling a reaction within the reaction chamber to generate the gas.

Preferably, the method comprises conditioning the generated gas. For example, any one or more of a humidity, temperature, pressure or flow rate of the gas may be monitored and/or controlled.

Preferably, the method comprises storing gas generated in a gas storage chamber.

Preferably, the method comprises providing gas generating material. This may be achieved by feeding gas generating material into the reaction chamber and/or replacing at least a portion of the reaction chamber with a replacement at least a portion of a reaction chamber, the replacement chamber containing replacement gas generating material. The replacement gas generating material may be provided in a cartridge such that replacement of the gas generating material is achieved by removing a cartridge containing depleted gas generating material and inserting a replacement cartridge containing new or reconditioned gas generating material.

Further features of this method are analogous to features described hereinabove and below, including those described with reference to insufflation apparatus. In particular, gas generation may be achieved as described previously.

Referring to all of the previous aspects, gas generated and used in an insufflation or other surgical procedure may subsequently be collected for reuse and/or for reconditioning or renewing the gas generating material. Additionally or alternatively, a by-product may be collected and used for similar purposes. Thus, the invention further provides a reusable or "rechargeable" gas generator or cartridge or insufflation apparatus.

For example, gas may be provided in the surgical procedure using a first conduit or first part of a conduit and collected using a second conduit or second part of the first conduit. The first and second parts of the conduit or the first and second conduits may be positioned such that they are adjacent or in close proximity to one another. This may enable, for example, both flows to be achieved via a single opening into a body cavity. However, preferably, separate openings into the relevant body cavity are provided whereby generated gas enters through a first opening and exits through a second opening. Preferably the first and second openings are spaced apart—as will be appreciated, the degree of spacing will be determined in part by the size of the relevant cavity and the convenience or ability to provide an opening in a given position. Such an arrangement is beneficial in promoting a circulation of gas through the cavity, which can be useful in preventing visual obstruction by smoke or other debris during a procedure.

At its simplest, the collected gas may simply be recycled back to the first conduit or first part of the conduit so that it is used again but preferably at least a step of filtering is performed to remove any smoke or other debris present in the gas.

According to one embodiment the recycled gas is fed into the gas storage chamber.

According to another embodiment, the recycled gas may be fed to a reaction chamber and/or a gas generating cartridge with the purpose of replenishing the same with gas generating material. Specific examples of such arrangements are provided herein below with reference to the drawings.

Again, referring to all of the previous aspects, control thereof will now be described in more detail.

For all embodiments, sensors may be positioned throughout the apparatus and the wider circuit used to deliver the generated gas to a patient, and where applicable, subsequent thereto where the gas is then collected. Such sensors may be configured to monitor the gas generation and/or parameters of the gas so that it has the required properties for the particular application. Thus any one or more of the following may be monitored: a temperature of the gas generating material and/or the chamber holding the gas generating material; a temperature and/or pressure and/or flow and/or humidity of the gas at any one or more points within the circuit; a rate of gas generation; or other properties of the generated gas such as a composition thereof. Other sensors may also be provided. For example, a sensor may detect insertion of a cartridge inside a mount of the insufflation apparatus—this may then trigger or otherwise be used to automatically initiate the generation of gas and/or control thereof. Sensors and/or a user interface may also be used to receive inputs from a user. When measuring pressure, due to the compressible nature of gases and the transport thereof in elongate circuits, a separate sensing conduit may be provided to monitor pressure at or near the patient. The sensing conduit preferably has a small diameter and/or relatively short length to reduce possible errors in readings.

One or more processors may be operatively connected to the sensors so as to receive signals therefrom. The one or more processors are preferably configured to control the gas generation and/or conditioning of the gas post-generation, so that the gas generation is at a satisfactory rate or amount and/or the gas has the required properties for the particular application. Thus control loops may be provided for maintaining characteristics of the gas generation and/or the gas within desired bands. Means and techniques for effecting such control will be familiar to those skilled in the art.

Various embodiments of the invention may be adapted to generate carbon dioxide, a nitrous oxide or oxygen, for example, although other gases are within the scope of the invention. Further, adaptation may be made to generate a gas mixture comprising two or more gas components or one or more gas components together with an additive such as a sterilizing agent and/or a drug. Thus references to "gas" and "generating gas" and the like throughout the specification include a single gas, a plurality of different gases and/or one or more gases and an additive, and generation of the same. For example, multiple first reactants and/or multiple second reactants may be provided in the same or separate reaction chambers or sub-chambers, with different pairings of the reactants resulting in the generation of different gases or providing the same gas via a different reaction or generation of an additive. Mixing means such as a manifold may be used to mix the different gases, particularly where they are generated in different reaction chambers. As another example, a single absorber/desorber or different absorbers/desorbers may be charged with different gases. Further, while the invention is described with particular reference to insufflation uses, it will be appreciated that alternative reactions may be used to generate respiratory gases, such as oxygen or oxygen-enriched streams used by ventilators or the like.

Further aspects of the invention, which should be considered in all its novel aspects, will become apparent from the following description.

BRIEF DESCRIPTION OF THE DRAWINGS

A number of embodiments of the invention will now be described by way of example with reference to the following drawings.

DETAILED DESCRIPTION OF THE PREFERRED EMBODIMENT

Figure 1:
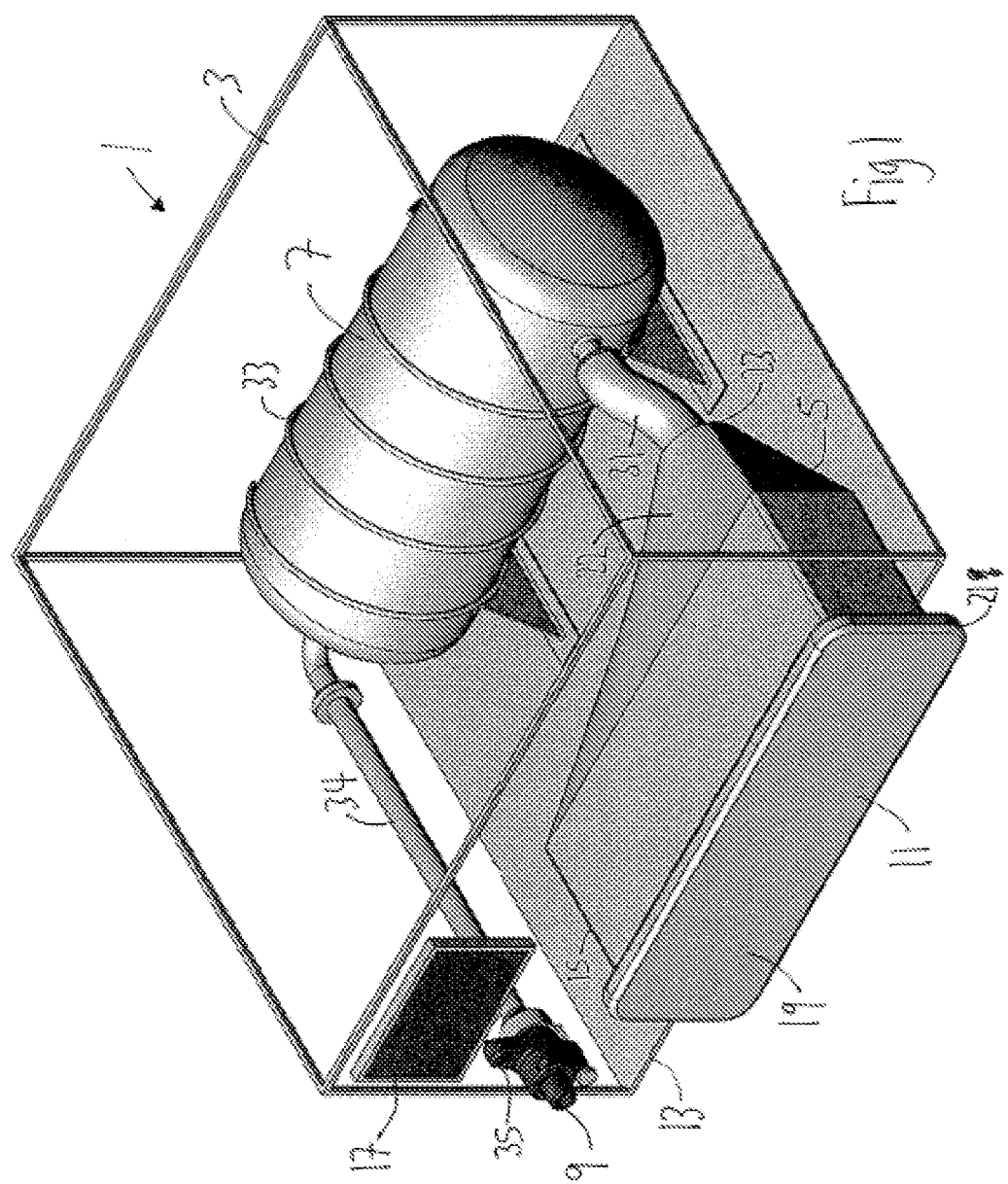
FIGS. 1 and 2 are perspective and plan views, respectively, of an insufflation apparatus and removable gas generating cartridge in accordance with the present invention, with the walls of the housing of the apparatus in outline only for clarity.
Figure 2:
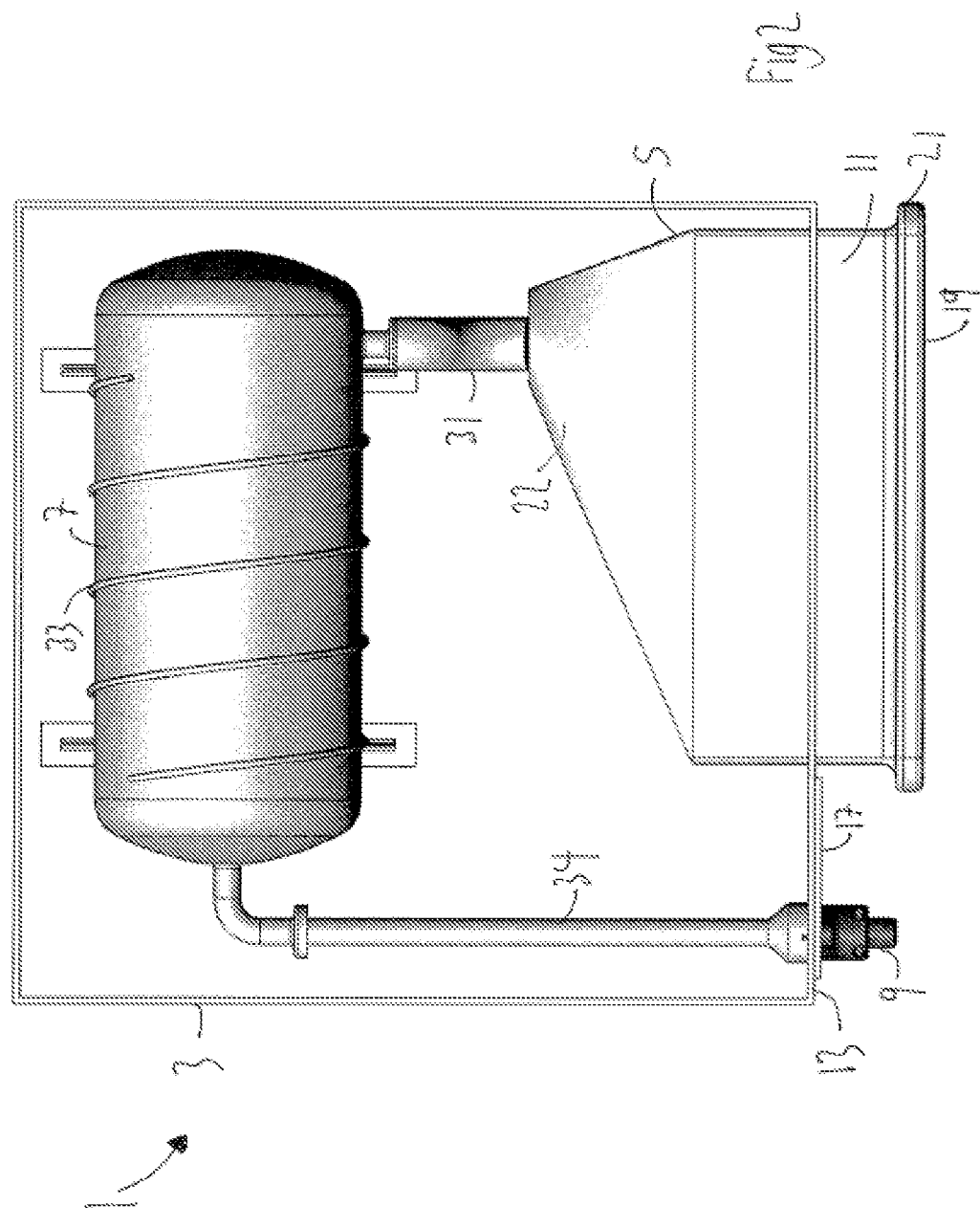
Figure 3:
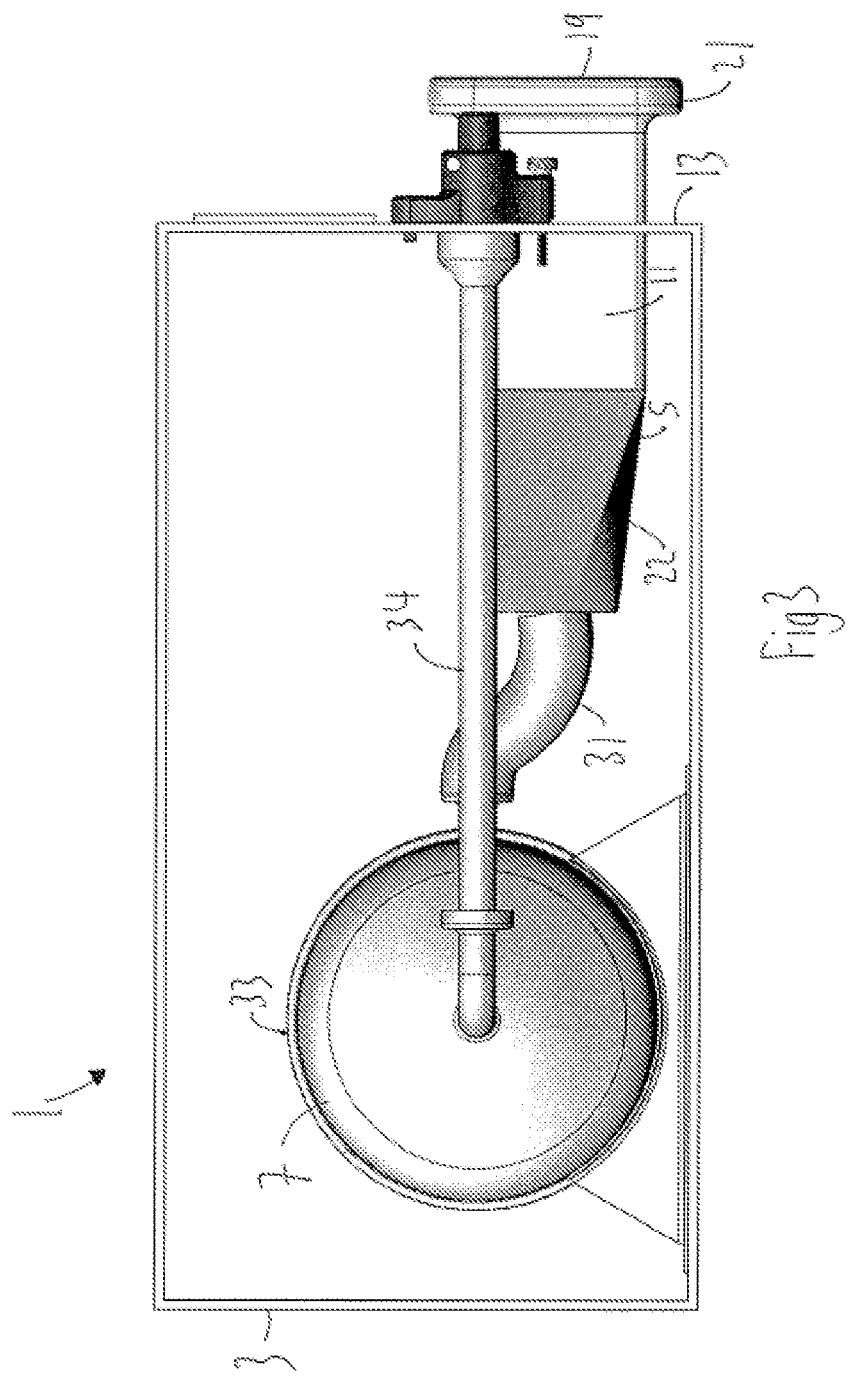
FIG. 3 is a view from one side of the apparatus of FIGS. 1 and 2.
Figure 4:
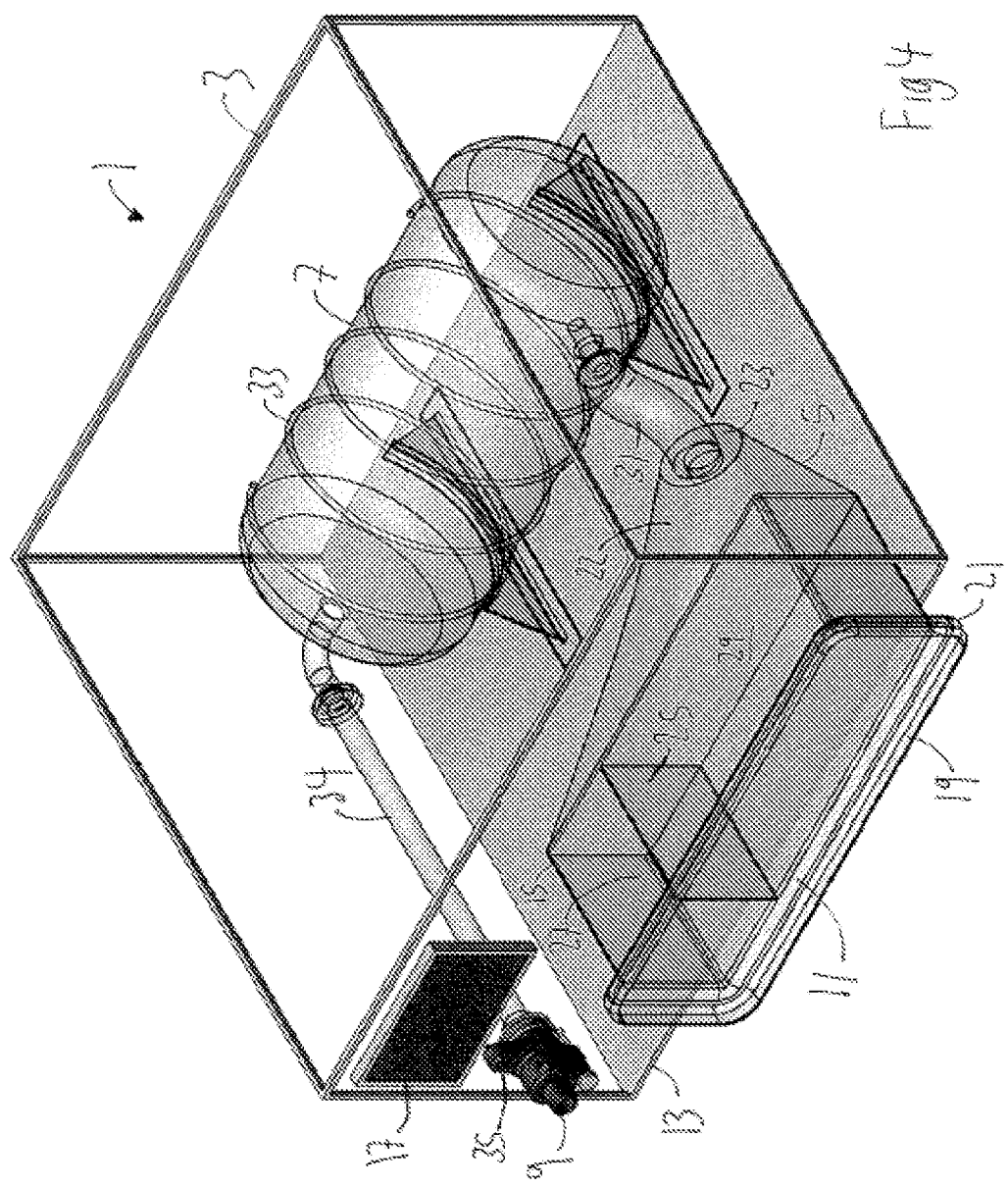
FIG. 4 is a perspective view of the apparatus of FIGS. 1 to 3 with the primary components shown in outline only such that the internal features can be seen.

Referring to FIGS. 1 to 4, an insufflation apparatus 1 comprises a housing 3 in which a cartridge mount 5, a gas storage chamber 7, and a gas outlet 9 are mounted, the gas outlet 9 being arranged to deliver gas to a body cavity of a patient. The cartridge mount 5 receives a gas generating cartridge 11 which is arranged to generate and deliver gas to the gas storage chamber 7 where the gas is stored, and immediately or subsequently delivered to the patient gas outlet 9. The outlet 9 is of suitable form to attach a gas delivery tube or cannula or the like to deliver the gas from the gas storage chamber to a body cavity of the patient as required. For example, the outlet 9 may be provided with a push fit, snap fit or locking connection onto which a cannula can be mounted.

The apparatus 1 is therefore a self-contained system having all of the primary components necessary to provide gas to a body cavity of a patient for insufflation, without requiring any remote, external separate gas connection. In particular, the apparatus 1 includes an integral source of insufflation gas which avoids the need to connect the apparatus 1 to a remote source of pressurized gas either temporarily or permanently. The apparatus 1 is therefore mobile and easily portable between locations, and can be used at any time without requiring a separate remote source of pressurized gas. It can in fact be used in locations which do not have a source of pressurized gas at all, such as in the field, for example.

The housing 3 in this example is cuboidal but may be any desired shape. A front face 13 of the housing 3 is provided with an oblong opening 15 comprising part of the cartridge mount 5, in which the cartridge 11 is received. In this example, the gas supply outlet 9 is also provided on the front wall 13 together with a user interface/display 17 of a controller (not shown). The user interface may take any form but in one example may comprise a touch screen display. As will be appreciated, the user interface may be otherwise positioned with data provided to and/or by an operator via wired and/or wireless communications. Thus the interface may be remote from the apparatus 1 and/or an additional interface may be provided remote from the apparatus 1, including for the purposes of reporting on the use or operation thereof.

The cartridge 11 in this example comprises an oblong body dimensioned to be inserted through the opening 15 in the housing 3. The front of the cartridge 11 comprises a front plate 19, the periphery of which projects beyond the margin of the body of the cartridge 11 to define a peripheral flange 21. This flange 21 may abut the front face 13 of the housing 3 to limit how far the cartridge 11 can be inserted into the housing 3. In this example, the interior of the cartridge 11 is divided, by partition 25 (see FIG. 4), into two sub-cavities 27, 29 each of which contains a respective material for gas generation. A rear part of the cartridge 11 is provided with a generated gas outlet (not shown) which forms a fluid connection with the gas storage chamber 7 via the cartridge mount 5.

The cartridge mount 5 comprises a cavity inside the housing 3, the front of the cavity comprising the oblong opening 15. The cavity comprises opposed side walls and opposed upper and lower walls arranged to engage, locate, orientate and support the cartridge 11. The internals walls may instead comprise cartridge supports such as fingers, rails, protrusions or the like which abut the cartridge 11 in use. The rear of the cartridge mount 5 in this example comprises a manifold 22 of frusto-conical form, the apex of which defines a manifold outlet 23. The manifold outlet 23 functions as a fluid connector which connects the generated gas outlet of the cartridge 11 to the gas storage chamber 7.

The manifold outlet 23 forms a fluid connection with the gas storage chamber 7 via a link conduit 31 extending between the rear of the cartridge mount 5 and an inlet end of the gas storage chamber 7.

The manifold 22 may instead be formed, at least in part, by the housing of the cartridge 11.

The gas storage chamber 7 comprises a cylindrical pressure vessel mounted across a rear part of the housing 3. In this example, the chamber 7 is provided with a chamber heater in the form of an external helical heating coil 33 extending around the chamber 7. Other forms of chamber heater may alternatively or additionally be used, including an internal heating coil, or a heating plate adjacent part of the chamber 7.

The chamber heater may be controlled by the controller to achieve a desired temperature of gas within the chamber 7. The heater may be controlled in dependence upon the availability of gas in the chamber 7, or the rate of delivery of gas to the chamber 7 from the cartridge 11, for example. A sensor may be provided to generate a signal indicative of gas flow into the chamber, this signal being used by the controller to activate the chamber heater. Alternatively or additionally, an operator may enter a desired gas temperature into the user interface so that the controller subsequently controls the chamber heater accordingly.

Gas from the gas storage chamber 7 is transferred to the gas outlet 9 via a supply conduit 34 extending from an outlet end of the chamber 7 to the front face of the housing 3.

The gas outlet 9 is provided with a supply control valve 35. This valve 35 may be controlled by the controller, and/or manually by the operator as required, to deliver the required flow rate/pressure of gas to the patient. Pressure and/or flow sensors may be provided to generate feedback signals to enable control to be effected.

A closure is provided on the cartridge 11 and arranged to separate the materials for gas generation stored in the cartridge 11, from one another and/or the ambient air, such that gas generation does not occur. The closure may comprise an actively controlled closure which is controlled by the controller and/or a passively controlled closure which automatically opens or is opened in a predetermined circumstance. More than one closure may be provided. Additional closures may be provided on the cartridge mount for example.

In one example, the closure may comprise a barrier seal across the generated gas outlet of the cartridge 11. The cartridge 11 or the cartridge mount 5 may be provided with a perforator such as a piercing or cutting element arranged to pierce or cut the barrier seal to open the closure. The piercing or cutting element may be arranged in the cartridge mount 5 such that it automatically pierces or cuts the barrier seal when the cartridge 11 is fully mounted on the cartridge mount 5. In one example, the cartridge 11 is pressed into the cartridge mount 5 which breaks the seal and causes gas generation to begin immediately. More particularly, the inlet to the gas storage chamber may comprise a substantially rigid conduit that extends out from the gas storage chamber so that it passes the seal on mounting or insertion of the cartridge. Alternatively, the perforator may be under the control of the controller such that the element pierces/cuts the seal at a selected time. For example, this may be when the operator sends an activation signal to the controller, or when a cannula or the like is connected to the patient supply outlet 9, a suitable cannula detection sensor being provided at the outlet 9.

In another example the closure may comprise a valve (e.g., but not limited to be a duckbill valve) or closure cap which closes the generated gas outlet of the cartridge. Again, the valve or closure cap may be arranged to open automatically when the cartridge 11 is fully mounted on the mount 5, or may be arranged to open or close under the control of the controller. In a further example, a compressor is between the gas storage chamber 7 and the cartridge 11. The compressor may be provided to urge gas into the gas storage chamber 7 so as to pressurize the contents. Additionally or alternatively, by creating reduced pressure on a downstream side of the closure, the compressor may be used to open the closure, for example, by causing it to rupture, deform or move to an open position.

In a further example, the closure may comprise or be provided with a partition or barrier wall between sub-chambers of the cartridge 11, where each sub-chamber contains a respective material for gas generation.

The closure may comprise multiple closure elements, one provided on the cartridge 11 itself, with another provided between the cartridge 11 and the gas storage chamber 7, for example, in the manifold 22 or the link conduit 31. Thus, a first part of the closure may be opened automatically when the cartridge 11 is mounted on the mount 5, with the second part of the closure being subsequently selectively opened or closed by the controller.

Where the closure is fully or partially selectively controlled by the controller, the controller may be arranged to control the rate of gas generation by controlling the degree of opening of the closure. The controller may be arranged to end gas generation at a desired time, by closing the closure after an initial period of gas generation.

The cartridge 11 is provided with one or more materials for gas generation. For example, two materials may be provided, such as aluminium carbonate and water to produce carbon dioxide. The one or more materials may be arranged to generate gas from a chemical reaction which occurs when the one or more materials are exposed to ambient air, or which occurs when two or more of the materials are exposed to one another. A combination of reactions may be provided whereby two or more of the materials react with each other and ambient air (or some other material including solids, gases or liquids).

The cartridge 11 may be arranged to be removable during or after gas generation without affecting the delivery of gas to the patient via the patient supply outlet 9. This may be achieved using an isolator. The isolator may comprise the closure, or a separate valve or closure between the cartridge 11 and cartridge mount 5. Thus, when the cartridge 11 is removed, the separate valve or closure is arranged to close such that generated gas cannot escape either from the cartridge 11, nor the cartridge mount 5. In this way, the apparatus 1 may be pre-charged with gas generated from the cartridge 11 before the apparatus 1 is used with a patient, the generated gas from the cartridge 11 being stored in the gas storage chamber 7 for subsequent use.

The generated gas from the cartridge 11 may result in a relatively high gas pressure within the cartridge 11 and cartridge mount 5. This pressure is preferably controlled such that the gas pressure at the patient supply outlet 9 is at a level suitable for delivery to the patient. The gas storage chamber 7 may itself function as an expansion chamber in which the highly pressurized gas from the cartridge 11 expands, reducing the gas pressure. The valve at the gas outlet 9 may be operative to control the gas pressure of gas emitted through the outlet 9, by restricting the gas flow. The controller may be arranged to monitor and control the valve to achieve the desired gas pressure. Additional flow restrictors and/or flow control valves may be provided in the gas flow path to further control the gas pressure. Likewise, the flow path itself may be arranged to reduce the gas pressure of gas from the storage chamber by defining a tortuous flow path, or by incorporating baffles or the like.

A humidifier (not shown) may optionally be provided, mounted on or inside the housing 3. The humidifier is arranged to provide fluid vapour to the gas flow, at some position in the gas flow path. In one example, the humidifier may be arranged to deliver fluid vapour to gas in the flow path from the gas storage chamber 7. The humidifier may comprise a passive or active humidifier. If active, the humidifier may comprise a humidifier heater and a humidifier vessel containing liquid to be heated by the heater, wherein the flow path comprises transportation through the humidifier vessel headspace between an inlet port and an outlet port of the vessel. The vessel may be removable for refilling with fluid. Additionally or alternatively, a closeable port may be provided. The controller may be arranged to control the level of heating and the level of vapour delivered to the gas to control the moisture content of the gas. The humidifier may be provided, at least in part, inside the housing 3.

The apparatus may further comprise a gas control heater assembly arranged to control the pressure and/or temperature of the gas. The gas control heater assembly is preferably provided in the housing, and may be positioned in the gas flow path between the cartridge 11 and the gas storage chamber 7, and/or in the gas flow path between the gas storage chamber 7 and the patient supply outlet 9. The gas control heater assembly may be controlled by the controller, either automatically according to a controller algorithm, or via operator input.

The gas control heater assembly may comprise a first heater arranged to control the pressure of the gas, and a second heater for controlling the temperature of the gas. The first and second heaters may be located in different parts of the gas flow path within the housing. Either of the first or second heater may comprise the heater provided at the gas storage chamber 7. Heaters may additionally or alternatively be provided downstream of the apparatus 1. For example, a conduit used to deliver gas from the apparatus 1 to a patient may be provided with a resistive wire heating element in or associated with the wall of the conduit to heat gas as it flows therethrough.

The controller of the apparatus 1 may take any suitable form and may include a display, an electronic data processor, temporary and/or permanent data storage, and suitable electronic circuitry. The controller may include one or more algorithms and/or data lookup tables to control the various components of the apparatus to achieve a particular flow rate, temperature and pressure of gas delivered to the patient. The algorithms may be arranged to achieve a predetermined flow rate, temperature and pressure of gas, or may be arranged to achieve an operator-selected flow rate, temperature and pressure of gas. The display may be arranged to display characteristics of the gas including one, some or all of flow rate, temperature and pressure of gas. The display may be further operative to display elapsed and remaining gas discharge time, and/or information on the discharge condition of the cartridge including, for example, when the cartridge is fully discharged. A visual and/or audible warning or warnings may be generated as the gas in the gas storage chamber 7 discharges, indicative of the time remaining before full discharge. This provides the operator with information on how much time remains before the gas runs out and a new cartridge must be inserted.

Figure 5:
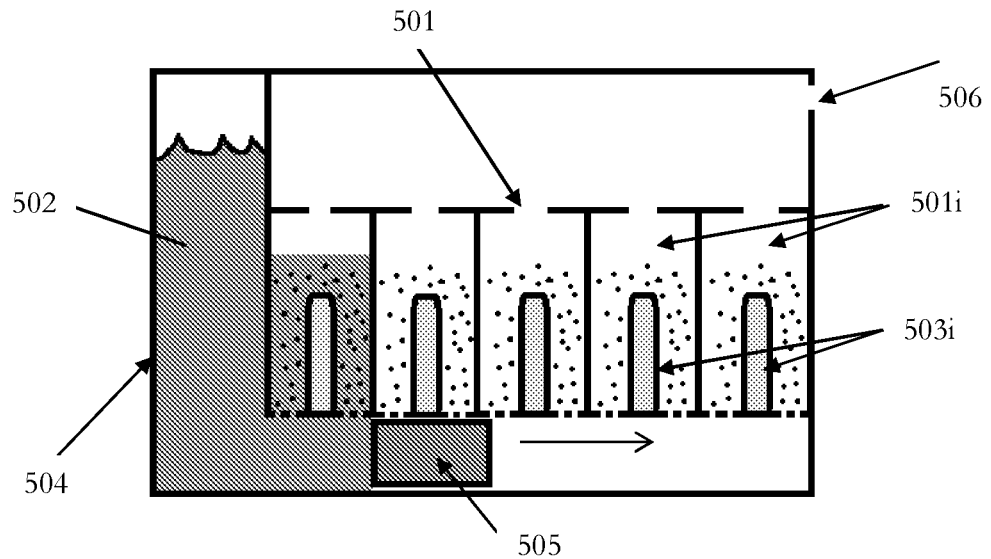
FIGS. 5 to 8 show alternative embodiments of a gas generating apparatus.

FIG. 5 is a sectional schematic view of an alternative gas generator. According to this embodiment, the gas generator comprises a reaction chamber 501, a first reactant 502 fluidly communicable with a second reactant 503. Preferably, the first reactant 502 may be selectively isolated from at least a portion of the second reactant 502 or vice versa.

The second reactant 503 is preferably provided in a manner so as to form a body although it may additionally or alternatively be formed as particulate or powder. According to the arrangement shown, the reaction chamber 501 includes a plurality of sub-chambers 501i that each include an elongate body or rod 503i of the second reactant. Other numbers of sub-chambers may be used or the reaction chamber may not be partitioned to form sub-chambers.

The first reactant 502 is shown as being stored in a reservoir portion 504 of the gas generator. Alternatively it may be stored in a reservoir remotely positioned but in fluid communication (preferably selectively via a valve or the like) with the reaction chamber 501.

The mixing of the reactants is preferably controlled to control initiation and ongoing maintenance of the reaction. For example, as shown in FIG. 5, moveable block 505 sealably engages about its perimeter to prevent flow of the first reactant 502 into one or more portions of the reaction chamber 501. In the position shown, four sub-chambers 501i are isolated from the first reactant 502 with the first reactant 502 present in the leftmost sub-chamber 501i via one or more apertures in the base thereof. As will be appreciated, as the block 505 moves towards the right hand side of the gas generator, fluid communication is established with additional sub-chambers, allowing the reactants 502, 503 to come into contact and initiating the reaction therein.

Alternative arrangements will be apparent. For example, the block 505 may be omitted and the apertures in the base selectively closed using valve members (not shown). Switching means may then be used to control opening of the valves as desired. Additionally or alternatively, the reaction chamber 501 may be fluidly connected to a compressor, such as via outlet 506, with the compressor configured to generate a reduced pressure and urge the block 505 to change its position. Reduced pressure within the reaction chamber 501 can also assist in encouraging evaporation of the liquid contents of the reaction chamber 501 to increase the humidity of the gas generated. Movable stops may be provided to limit movement of the block 505 such that it can only move when allowed. For example, the stops may extend into the path of the block 505 but be movable to a position whereby they do not obstruct the path of the block 505. This may be effected manually or via control and actuation circuitry.

Further, the reaction may be initiated by moving the second reactant 503 rather than or in addition to through movement of the first reactant 502. For example, the first reactant 502 could be provided in all sub-chambers 501a-501e with the second reactant 503 being introduced therein via a closeable aperture or by lowering the second reactant 503 into contact with the first reactant 502 from the headspace inside the reaction chamber. Such arrangements would also function without partitioning of the reaction chamber 501 into sub-chambers 501i. Alternatively, with the apparatus configured as shown in FIG. 5, means may be provided for inserting additional second reactant 503 material into the reaction chamber 501 such as via closeable ports in the roof thereof.

For the embodiment of FIG. 5, when configured to produce carbon dioxide, the first reactant 502 may comprise water and/or an aqueous solution and/or an acid and/or an acid-based solution. The second reactant 503 may comprise a carbonate material such as aluminium bicarbonate or sodium bicarbonate. Other reactants may be used to produce other gases or to produce carbon dioxide.

As shown in FIG. 5, the second reactant 503 is shown formed as a body or rod. Such an arrangement can provide for a relatively slow but sustained reaction. To increase the rate of reaction during the early stages thereof, particulate or at least smaller bodies formed from the second reactant 503 may also be present. Alternatively, the second reactant may be formed entirely from particles or powder or at least smaller bodies.

Heater means may be provided to heat the contents of the reaction chamber 501 to increase the rate of reaction. For example, the insufflation apparatus may comprise a heater plate onto which the reaction chamber 501 and/or the reservoir portion 504 is received. Additionally or alternatively a heater element may extend into the reaction chamber 501 and/or the reservoir portion 504. Other external heating means may additionally or alternatively be used. For example, the reaction chamber 501 and/or the reservoir portion 504 may be at least partially circumscribed by one or more heater coils.

Gas generated in the reaction chamber 501 may be allowed to exit via outlet 506 and then be processed in a similar manner to that shown in FIGS. 1-4. For example, it may be stored in a gas storage chamber and/or treated to have desired properties. Thus the embodiment of FIG. 5 may simply provide for an alternative gas generator portion of the insufflation apparatus of FIGS. 1-4. More particularly, the gas generator of FIG. 5 may be configured as a removable cartridge that connects to form an insufflation apparatus in a similar manner to that shown in FIGS. 1-4. Alternatively, only a portion the gas generator of FIG. 5 may be in the form of a cartridge. For example, the reaction chamber 501 may be removable with the reservoir portion 504 forming a more integral part of the insufflation apparatus, in which case ports may be provided for draining and/or filling the reservoir portion 504 with the first reactant 502. Additionally or alternatively, the reservoir portion 504 may be separately removable from the insufflation apparatus with a selectively closeable port provided for controlling opening thereof when the reservoir portion is connected to the insufflation apparatus. Alternatively, one or more sub-chambers 501i may be individually removable with the benefit that reactions may be occurring in one or more other sub-chambers 501i while a particular sub-chamber 501i is replaced.

Figure 6:
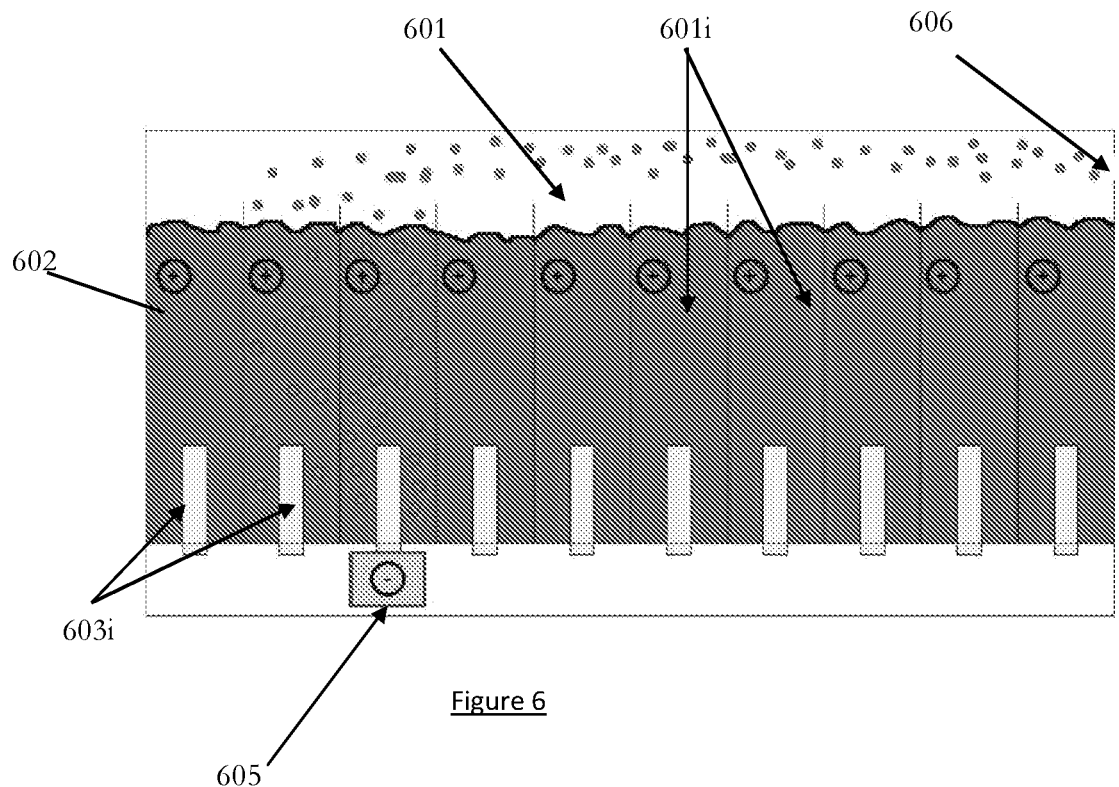

FIG. 6 shows a sectional schematic view of an alternative embodiment of a gas generator. According to this embodiment, gas is generated as a result of electrolysis. More particularly, charge may be applied via electrodes 603i, preferably copper electrodes, resulting in the decomposition of components of the solution 602 provided inside the reaction chamber 601. The solution 602 may comprise a carbon dioxide loaded amines solution (e.g., Piperazine or Diethanolamine), for example, although other solutions may be used, particularly for generating other gases. Such a solution releases carbon dioxide when an electromagnetic field is applied thereto via the electrodes. More particularly, the chains binding the carbon dioxide molecules to the amines are broken. The rate of reaction may be increased or decreased by increasing or decreasing, respectively, the voltage potential applied. Further, the number of electrodes in use may be varied.

In the embodiment shown in FIG. 6, a portion of each electrode 603i extends out of the reaction chamber 601 to enable electrical coupling thereof to a power supply via moveable block 605. Other arrangements may also be used. For example, each electrode may be connected to a power supply via a switching circuit such that any one or more of the electrodes may be activated at any point in time. Thus, to provide for more rapid gas production during early stages of the process, a first number of electrodes may be used initially and a second, fewer number of electrodes used once operational levels of gas are able to be produced through use of only the second, fewer number of electrodes.

In the embodiment shown in FIG. 6, the reaction chamber is partitioned into a plurality of sub-chambers 601i. Other numbers of partitions may be provided or the partitioning may be omitted.

Gas generated in the reaction chamber 601 may be allowed to exit via outlet 606 and then be processed in a similar manner to that shown in FIGS. 1-4. Thus, the gas generator of FIG. 6 may be incorporated into the insufflation apparatus of FIGS. 1-4 in a similar manner to the gas generator of FIG. 5.

Figure 7:
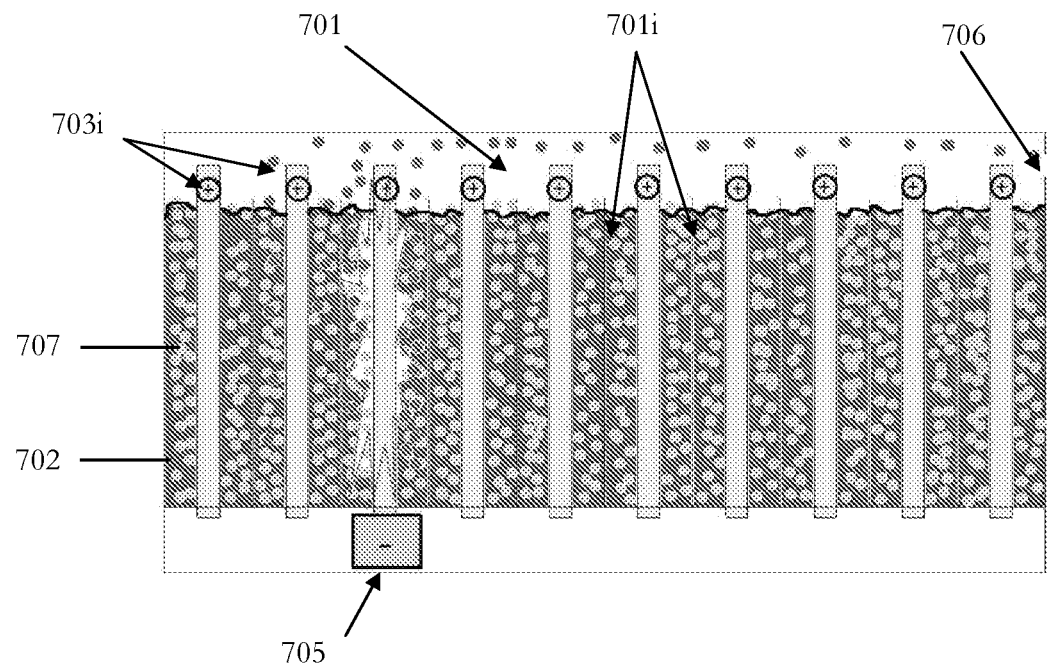

FIG. 7 shows a sectional schematic view of a further alternative embodiment of a gas generator. According to this embodiment, gas is stored in an absorber/desorber 707 with means being provided for causing desorption of the gas from the absorber/desorber 707.

Referring to FIG. 7, the reaction chamber 701 is at least partially filled with a medium 702 which may comprise water or an aqueous solution, by way of non-limiting example. While any absorber/desorber 707 appropriate for the gas to be generated may be used, according to a presently preferred embodiment, a microporous metal organic framework is used. For example, the framework may be formed from mmen-Mg2 or Cu-BTC, by way of non-limiting example.

Heater elements 703i are provided to cause the release of gas from the absorber/desorber. More particularly, through application of a voltage to one or more of the heater elements 703i, the temperature thereabout is increased, causing the gas to separate from the absorber/desorber 707. Increasing or decreasing the voltage applied and therefore the resultant temperature can increase or decrease, respectively, the rate of gas generation.

The embodiment shown in FIG. 7 includes moveable block 705 for effecting electrical coupling of at least one of the heater elements 703i to a power supply. Other means may be used to couple the heater elements 703i to a power supply. For example, each heater element may be selectively coupled to a power supply via a switch.

Again, the reaction chamber 701 is shown comprising sub-chambers 701i. Other numbers of sub-chambers may be used or partitioning may not be used. Partitioning in this and the other embodiments can be used to better control the rate of gas production throughout the use of the gas generator since each sub-chamber will perform in a similar manner to other sub-chambers of the same reaction chamber provided they are similarly configured. However, different configurations may be used for different sub-chambers. For example, some sub-chambers may be configured to produce a higher rate of gas generation than others such that the higher rate of reaction sub-chamber(s) are used during start up to more quickly generate gas, and then the slower rate of reaction sub-chambers used subsequently to provide a more sustained or prolonged release of gas. As will be appreciated, the need for these variations will be mitigated by provision of the gas storage chamber.

The gas produced may exit via outlet 706 and then be processed in a similar manner to that shown in FIGS. 1-4. Thus, the gas generator of FIG. 7 may be incorporated into the insufflation apparatus of FIGS. 1-4 in a similar manner to the gas generator of FIGS. 5 and 6.

Figure 8:
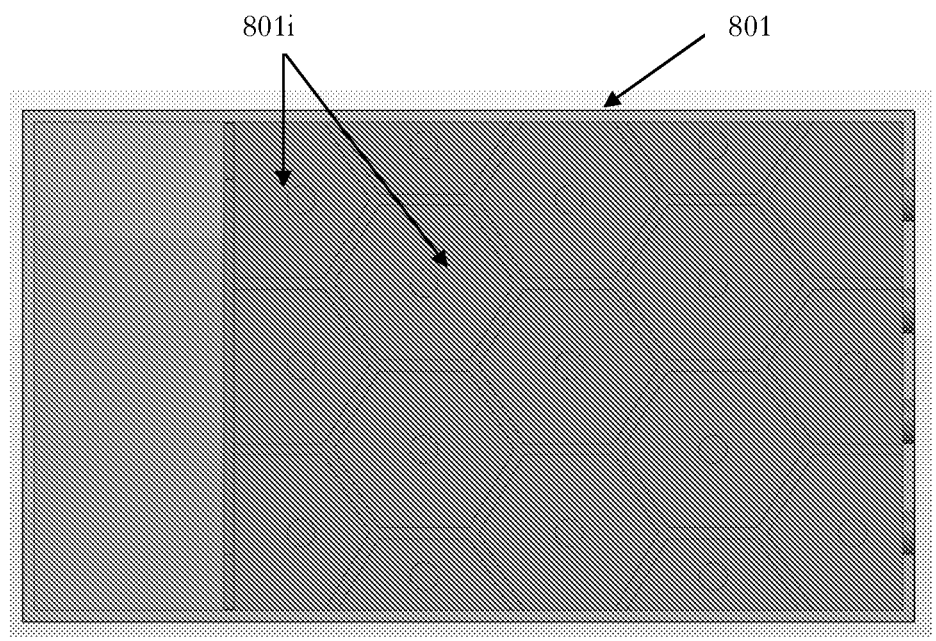

The plan view of FIG. 8 shows an alternative manner of partitioning of a reaction chamber 801. According to this embodiment, the sub-chambers 801i are in the form of hexagonal cells, similar to a beehive structure, allowing for a plurality of sub-chambers 801i to be more densely packed together. Other sub-chamber configurations may alternatively be used. Further, such configurations may be used for any of the embodiments shown in FIGS. 5-7.

Figure 9:
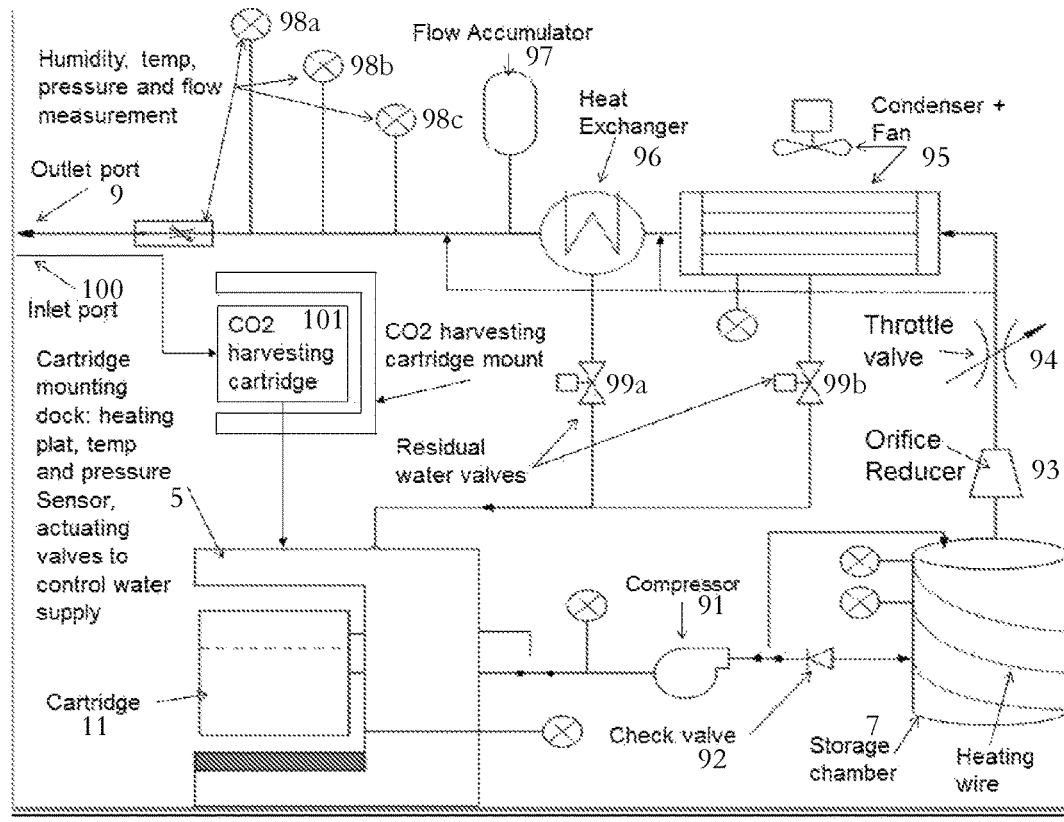
FIG. 9 is a schematic representation of an embodiment of an insufflation apparatus with FIG. 10 showing a broadly analogous schematic circuit or control diagram.

FIG. 9 is a schematic representation of an embodiment of an insufflator apparatus. Referring to FIG. 9, the apparatus 1 includes a gas generating cartridge 11 engaged in a cartridge mount or dock 5. The cartridge 11 is fluidly coupled to outlet port 9. While additional means are shown along the path from the cartridge 11 to the outlet 9, it will be appreciated that while such means are preferred, they are not essential and gas generated by the cartridge 11 may be used to directly expel gas to the outlet 9. The additional means may be provided to treat the gas generated so as to optimize it for a particular application. For example, any one or more of temperature, humidity, pressure or flow of the gas may be controlled. Additionally or alternatively, additional ports may be provided such that additives may be introduced into the gas stream. Further, to ensure gas is more readily available and to prevent interruptions in the supply of the gas to the outlet, preferably gas storage is provided for. Thus the system shown in FIG. 9 is merely an embodiment of the invention and should not be interpreted as limiting the scope to include all of the elements shown.

Referring to FIG. 9, gas generated in or by the cartridge 11 is fed to a compressor or flow enhancer 91 and then to storage chamber 7. Check valve 92 prevents the backflow of the gas out of the storage chamber 7. Gas may be collected and held in the storage chamber 7 prior to use of the system in a surgical or other procedure. As will be appreciated, there may be a lag between initiating gas generation and having a useful amount of the gas available at the outlet 9 for a given procedure. The storage chamber 7 allows this problem to be overcome, making gas readily available on commencement of a procedure.

Gas exiting the storage chamber 7 may pass through an orifice reducer 93 and/or a throttle valve 94 so as to control the flow of the gas. Condenser 95 may be used to reduce the humidity of the gas, as required. When not required, or when only a small amount of moisture needs to be removed, at least a portion of the gas may bypass the condenser 95, as shown by the dotted line.

Heat exchanger 96 may then be used to control the temperature of the gas, preferably by increasing the temperature. Again, this element may be bypassed as shown by the dotted line.

Flow accumulator 97 may be used to increase or reduce pressure as required.

Various sensors 98a, 98b, 98c are shown for monitoring properties of the gas prior to exiting through the outlet. These properties may include, by way of non-limiting example, any one or more of humidity, temperature, pressure or flow. One or more sensors may additionally or alternatively monitor a composition of the gas stream. For example, where multiple components are included in the gas, at least one component thereof may be monitored. For example, the proportion of the gas stream being formed by carbon dioxide may be monitored.

These or similar sensors may be positioned elsewhere within the system. For example, temperature and/or humidity may be monitored at various points throughout the circuit to provide for more rapid adjustment of these properties and to control switching of the circuit and/or components thereof. For example, control loops may provide for the switching of gas flow to bypass the condenser 95 if the humidity does not need to be reduced. Alternatively, heat provided by the heat exchanger 96 may be reduced or the heat exchanger 96 may be bypassed if the gas has a sufficiently high temperature.

Drains 99a, 99b allow any excess water to be removed from the heat exchanger 96 and the condenser 95. Where water is used as a reactant, at least a portion of this water may be fed back to a reaction chamber of the cartridge 11 and/or the cartridge mount 5.

FIG. 9 further shows an inlet port 100 and a gas harvesting cartridge 101. In many surgical procedures, it is common to "clean" the area being operated on by purging gas through said area. Thus, gas may be expelled through outlet port 9 into the area and vented into inlet port 100. Due to the pressurized nature of the gas stream, suction at the inlet 100 is not generally required but may be provided for. For example, the inlet 100 may be fluidly coupled to a compressor, such as flow enhancer 91. Debris, fluids and/or smoke or other gases may be expelled from the area and a filter may be provided to remove at least a portion of these from the gas stream.

The gas harvesting cartridge 101 may take any form or may be dispensed with. For example, for laparoscopic procedures and the like, the gas stream fed to the inlet will have a composition very similar to that passing through the outlet port 9. Thus the gas may simply be recycled to the outlet port 9, preferably following filtering. Additionally or alternatively, the recycled gas may be fed to the gas storage chamber 7 so that it may be processed or reconditioned to have required properties. Additionally or alternatively, it may be fed to another part of the circuit, depending on detected properties of the gas entering the inlet 100 and the determined processing steps required to accordingly condition the gas. Thus sensors may be provided to monitor properties of the gas entering the inlet port 100.

According to one embodiment, the gas harvesting cartridge 101 is used to extract at least one gas component of the gas stream so that it may be used for subsequent gas generation. Conveniently, this may be the same gas generated by the gas generating cartridge 11. More conveniently, the gas harvesting cartridge 101 may be formed in substantially the same manner as the gas generating cartridge 7. Consequently, on depletion of reactants within the gas generating cartridge 11, it may be removed and replaced with the gas harvesting cartridge 101. The original gas generating cartridge 11 may then be switched to harvest gas such that it becomes replenished with gas generating material.

It will be appreciated that the mechanical removal and replacement of cartridges in this way may be avoided by controlling the flow of gas within the system. More particularly, the flow of gas from the inlet port may be diverted, at least in part, to the gas generating cartridge 11 from the gas harvesting cartridge 101 and/or the outlet port 9 may be fed by the gas harvesting cartridge 101 rather than the gas generating cartridge 11. Thus, where the cartridge operates using a reversible reaction, the functionality may be reversed to provide for more continuous gas generation without the need for external supply of gas generating material. However, preferably at least one of said cartridges is removable to provide for replacement as required. Additionally or alternatively, at least one cartridge may include a port for receiving gas generating material, in which case, at least one cartridge may form an integral part of the apparatus and not be removable.

Further, rather than feed recycled gas to the separate gas harvesting cartridge 101, the gas may be fed to the gas generating cartridge 11. As desired, a gas storage chamber may store the gas prior to feeding it to the gas generating cartridge 11. For example, it may be preferable in some cases to maintain the gas generating cartridge in a gas generating mode with recycled gas being fed thereto during "downtime" when gas is not required at the outlet 9.

Examples of gas cartridge arrangements which may be configured to be replenished are shown in FIGS. 6 to 8. Referring more specifically to FIG. 6, when used for the production of carbon dioxide and with electrodes formed from copper, when the voltage is no longer applied to the electrodes 603i, the copper that bonded with the amines chains following release of the carbon dioxide during gas generation breaks apart from the amines chains. Carbon dioxide fed into the reactor is then able to bind to the amines chains, replenishing the reactor. Similarly, in the arrangement of FIG. 7, carbon dioxide recirculated into the reactor is able to bind again with the absorber/desorber 707. Again, the arrangements may be adapted to use different materials and/or reactants or other gas generating material. Further a sparger or similar means may be used to disperse the recycled gas throughout at least a portion of the reactor.

Further, rather than a single gas generating cartridge 11 being used, two or more cartridge mounting docks 5 may be provided that are configured to operate in parallel. Such embodiments may be used to ensure that gas is able to be generated using a second gas generating cartridge when a first gas generating cartridge is depleted of gas generating material. The second gas generating cartridge may be configured similar to the first gas generating cartridge or may be more compact, merely providing for sufficient gas generation to cover removal and replacement of the first gas generating cartridge. This may reduce the need for the gas storage chamber 7, but its inclusion is still preferred so as to enable more rapid changes (particularly increases) in flow and/or pressure to be provided at the outlet 9.

The gas storage chamber 7 is shown as being provided with a heating coil 33 to control the temperature of the gas. Preferably, additional heating is provided around the circuit to provide further control. For example, conduits used to transport gas from one element of the circuit to the next may be heated and/or cooled as required. Additionally or alternatively, thermal insulation may be provided. Further, other elements of the circuit may be provided with heating and/or cooling as desired. Thermal insulation may additionally or alternatively be provided as desired.

Figure 10:
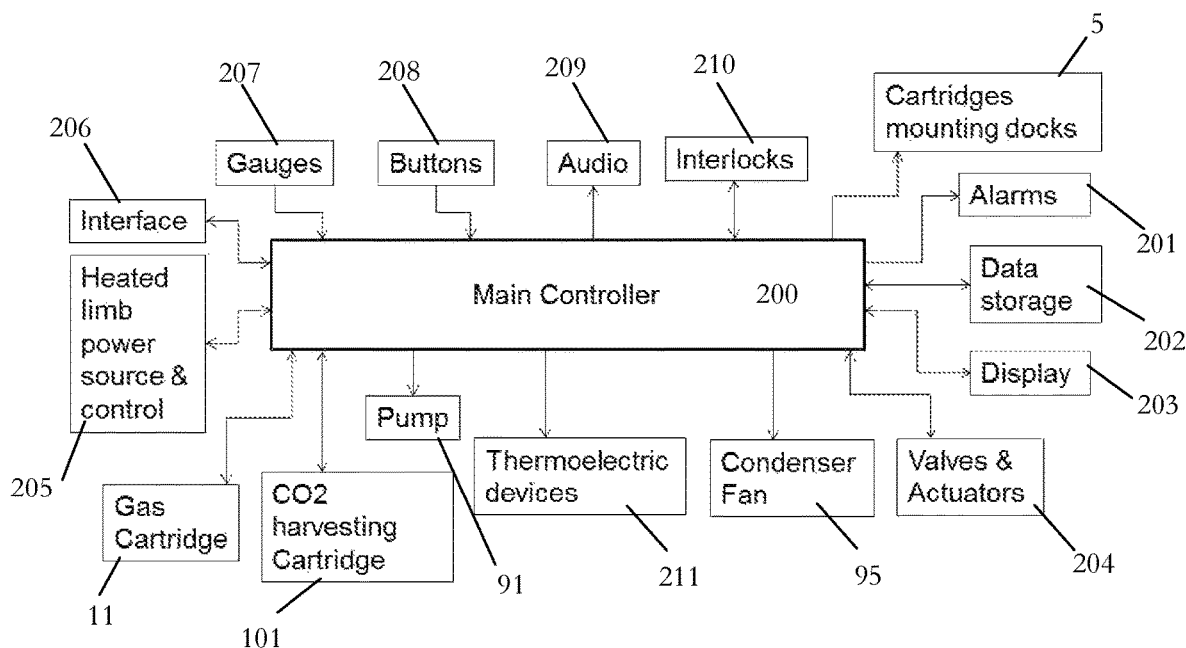

A schematic circuit or control diagram, generally corresponding to the more physical schematic of FIG. 9, is provided in FIG. 10. The circuit includes a main controller 200 configured to receives inputs from or transmit signals to other components of the circuit. The main controller 200 preferably comprises at least a processor and a memory containing logic defining control algorithms for the circuit. As will be appreciated, the main controller 200 may be formed by a single integrated unit or be distributed across a number of separate but communicatively coupled controllers. A mix of control types may also be used. For example, the main controller 200 may issue a command to a component of the system (or to a local controller for that component) to perform a particular task, and then performance of that task may be locally controlled by a separate controller; more particularly, the main controller 200 may command the compressor 91 to generate a particular pressure with subsequent control of the compressor 91 (such as fan speed) being controlled by a controller of the compressor 91 based on feedback received from sensors associated with the compressor 91 to achieve the desired pressure, responding to, for example, variations in the rate of gas generation. Further, connections between the main controller 200 and other components of the system may take any form including wired and wireless types.

The circuit includes elements described with reference to the preceding figures, such as cartridge mounting docks 5, condenser fan 95, pump 91, carbon dioxide harvesting cartridge 101 and gas cartridge 11. The main controller 200 may be configured to issue commands to these components to control their operation including the activation or deactivation thereof. The commands may be based in part on signals received from other components of the system (e.g., buttons 208, interlocks 210, valves and actuators 204, thermoelectric devices 211, or heated limb power source and control 205) or from the same components; for example, the gas cartridge 11 may signal to the main controller 200 that a particular sub-chamber is depleted of reactants and the main controller 200 may then issue a command so that the gas cartridge 11 activates a different sub-chamber.

Buttons 208 or other user input devices may be used by a user to make adjustments to the operation of the apparatus. Further, interface 206, gauges 207, audio output 209, alarms 201 and display 203 may generate visual and/or audible signals for a user informing of parameters of the apparatus and/or that there is a fault or some other problem, e.g., that the reactants are becoming depleted and that a gas generating cartridge 11 needs replacing or replenishing of reactants. Data storage 202 may be used to log data relating to errors and/or operating parameters of the system.

It will be noted that various components of the circuit shown in FIG. 10 may be omitted. Those included will depend on the apparatus set up for a particular application as well as user preferences.

Figure 11:
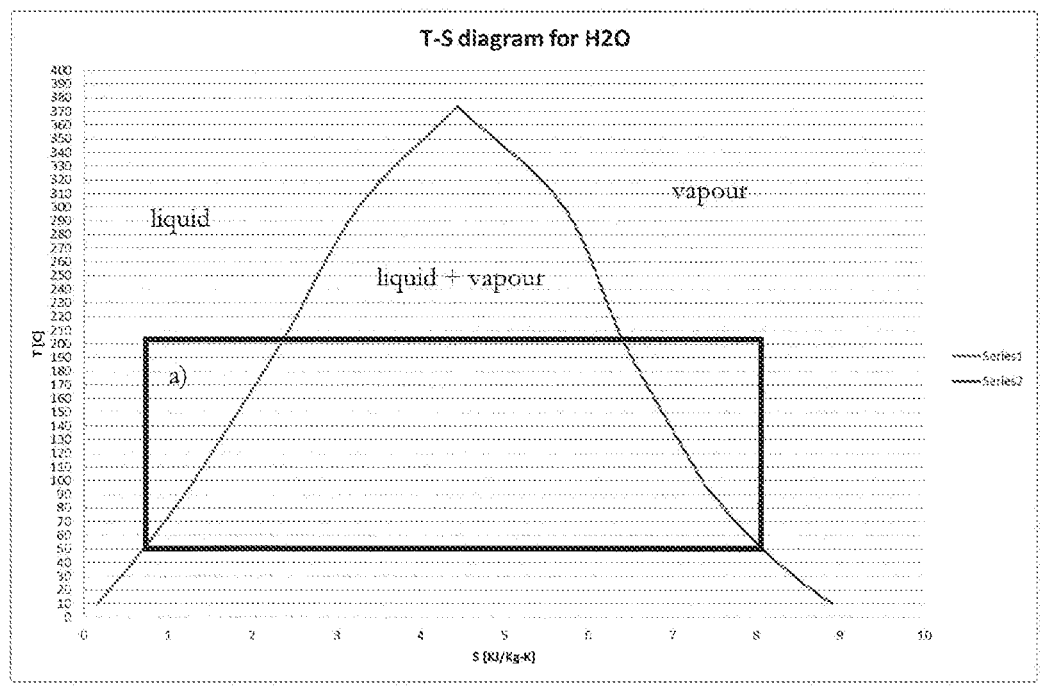
FIGS. 11 to 13 are temperature-entropy diagrams showing example conditioning of gas generated in accordance with the invention.

Example control implementation will now be described with reference to the temperature-entropy diagrams for water shown in FIGS. 11 to 13. Referring to FIG. 11, in the "liquid+vapour" stage, there is saturation and droplets of liquid will be present. In the "vapour" stage, no droplets are present and the humidity will be less than 100%.

Figure 12:
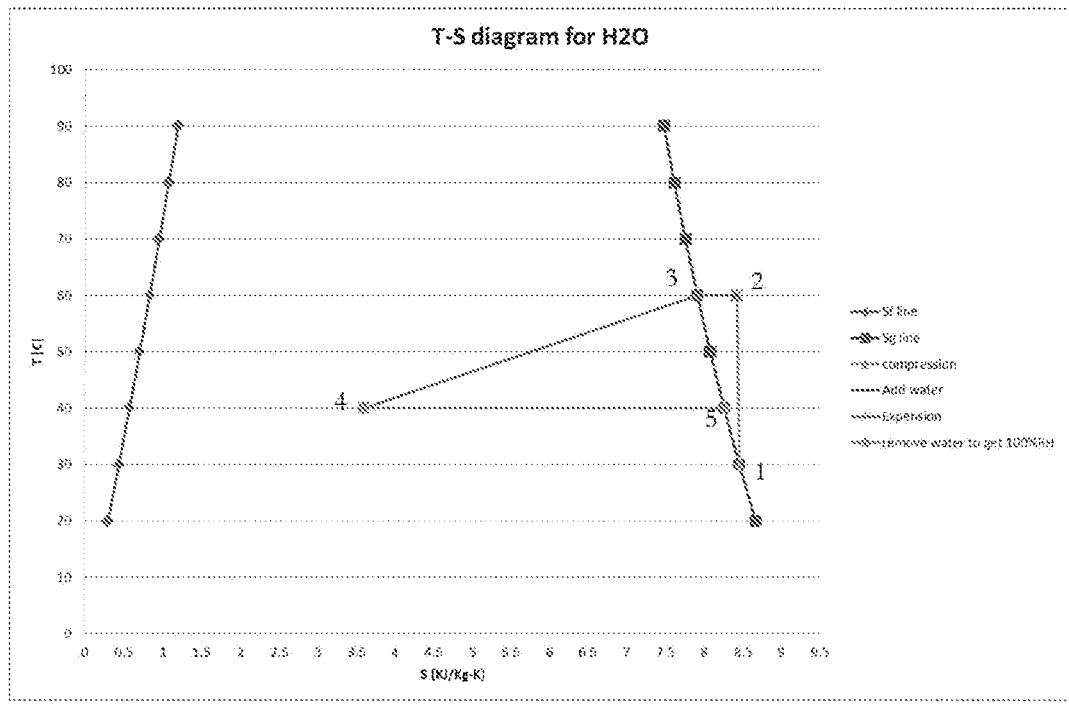

FIG. 12 shows the region (a) of FIG. 11 in more detail and shows a process of reducing relative humidity. At an initial temperature of 40° C. and relative humidity of 100% at point 1, the gas is cooled to 20° C. at point 2, resulting in condensation forming From point 2 to 3, the condensation is drained and then heat is applied such that the gas is again at 40° C. at point 4.

Figure 13:
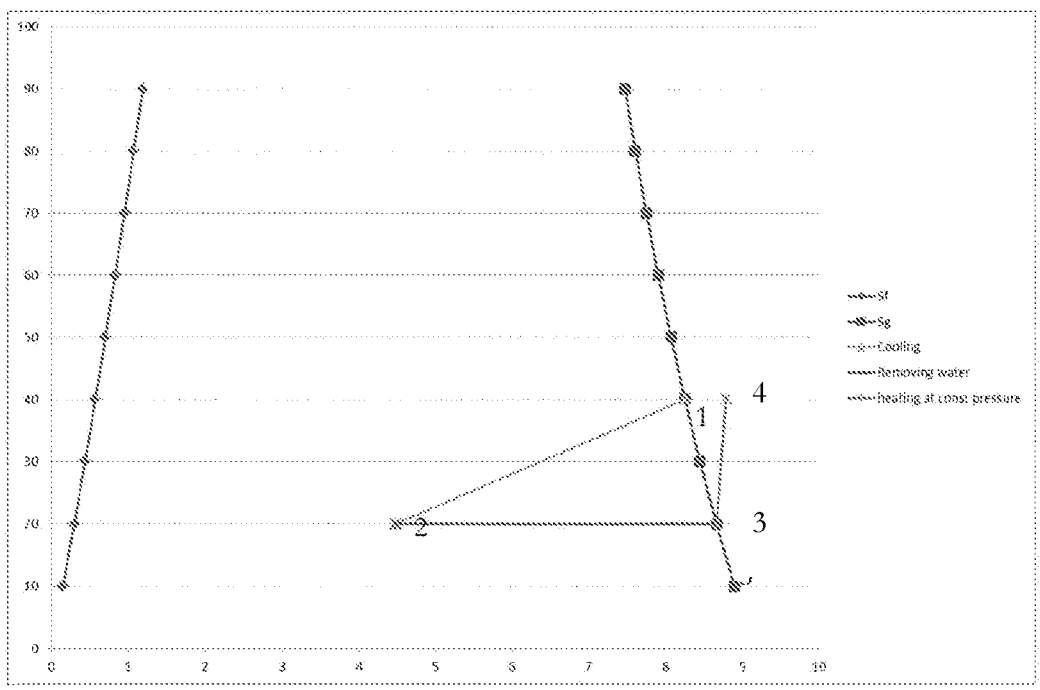

FIG. 13 shows an alternative sequence of operations that may be used to increase the temperature of the gas. Initially, at point 1, the gas is at 30° C. and relative humidity of 100%. The application of heat moves the gas to point 2 with a temperature of 60° C. at which point water is added to reach point 3. Cooling to point 4 (40° C.) and then draining to point 5 result in an increased temperature of 40° C. with 100% humidity maintained.

For the avoidance of doubt, the invention extends to both exothermic and endothermic reactions. Further, an exothermic reaction may be used not to generate gas but simply to generate heat to increase the temperature in the reaction chamber. This heat may then be used in a reaction used to generate insufflation gas.

Experimental Results

Testing was performed using a reaction to generate carbon dioxide. More particularly, 400 g of sodium bicarbonate and 200 g of citric acid were introduced into a cylindrical reaction chamber. These were mixed and the reaction was initiated by adding 60 ml of hot water. The reaction chamber was connected to a manifold (a heated standard aluminium pneumatic distributor) to capture gas generated and to direct it to a storage tank (a Festo air reservoir tank). Flow was measured using a CPS flow meter and carbon dioxide concentration was measured using a CheckMate $CO_2$ concentration tester, with the data therefrom logged using a LabView SignalExpress logger.

Figure 14A:
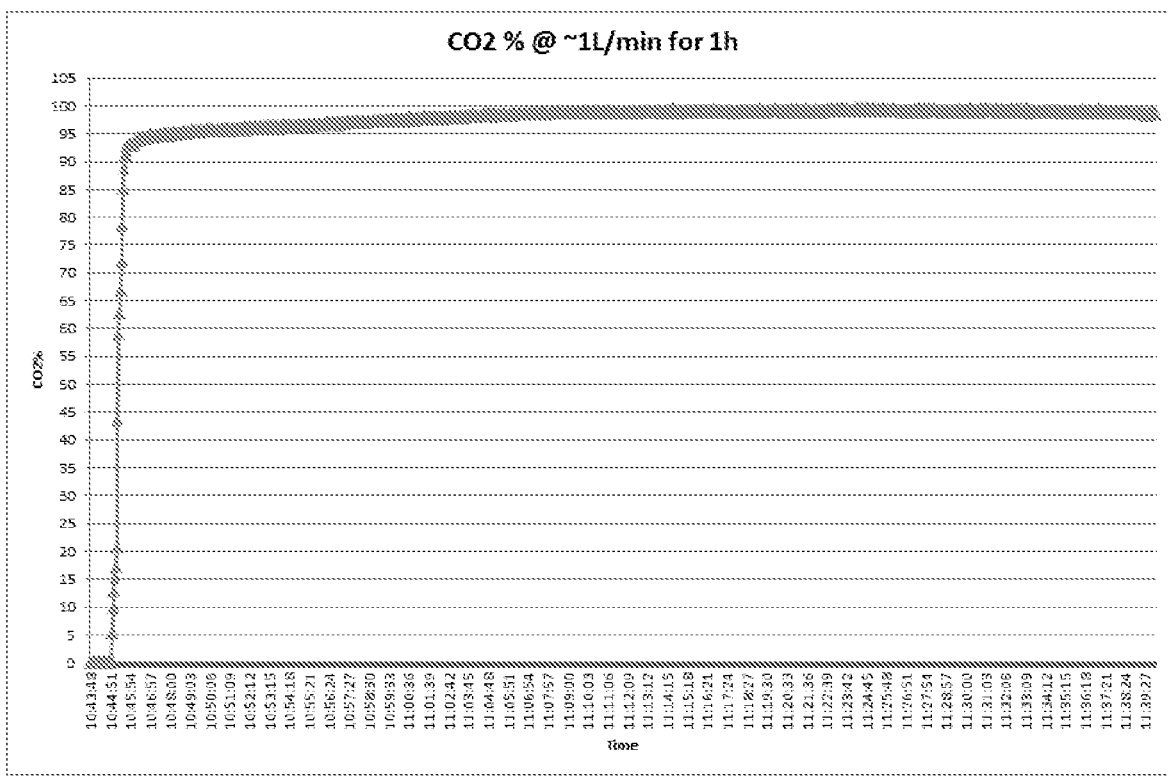
FIGS. 14*a* and 14*b* show experimental results obtained from a prototype arrangement.
Figure 14B:
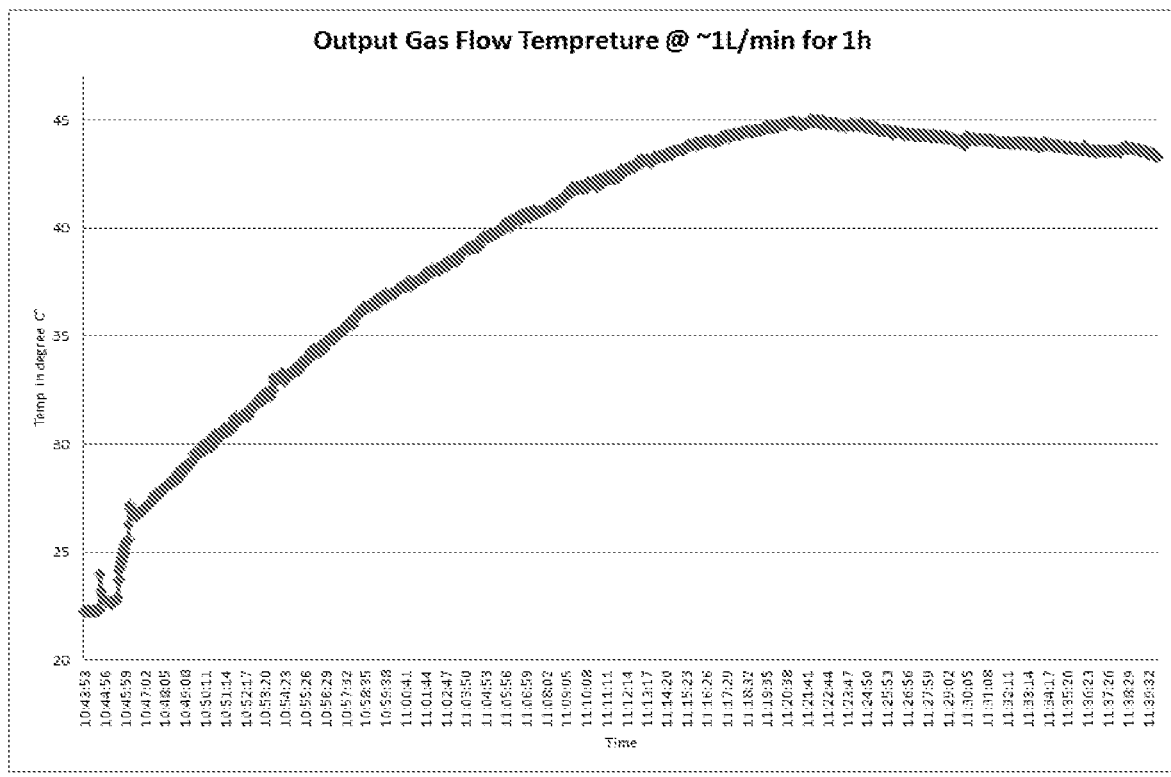

Immediately after adding the water, carbon dioxide production began and resulted in an increase in pressure in both the reaction vessel and the storage tank. The logged concentrations are shown in FIG. 14a and the temperature of the flow stream shown in FIG. 14b. As shown in FIG. 14a, the concentration of gas flowing from the reaction chamber quickly approached 100% carbon dioxide and this was sustained for almost an hour. Flow was maintained at about 1 L/min for the duration of the experiment with the temperature of the stream rising to 40° C. in about 20 minutes before peaking at about 45° C. and then slowly decreasing as the reactants became spent.

The experiment shows that it is readily possible to generate a high concentration of heated (and humidified) carbon dioxide using a chemical reaction. Further, even with a relatively simple arrangement, it was possible to generate a fairly constant gas flow for about 60 minutes. Additionally, condensed droplets were observed in the outlet gas pipes indicating that the gas had increased humidity.

Unless the context clearly requires otherwise, throughout the description, the words "comprise", "comprising", and the like, are to be construed in an inclusive sense as opposed to an exclusive or exhaustive sense, that is to say, in the sense of "including, but not limited to".

Although this invention has been described by way of example and with reference to possible embodiments thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

What is claimed is:

1. An insufflation apparatus comprising:
    a housing comprising a gas outlet for delivering gas to a patient; and
    a gas generator arranged to be, at least partially, mounted on or in the housing, the gas generator comprising:
        a gas storage chamber configured for storing gas and delivering gas to a body cavity of a patient via the gas outlet;
        a first cartridge mount on the housing adapted to receive a gas generating cartridge, the gas generating cartridge containing one or more gas generating materials reactive with one another to generate gas, wherein the gas generating cartridge, the first cartridge mount, and the gas storage chamber are arranged so that, in use, when the insufflation apparatus is in an active mode, the gas generating cartridge is in fluid communication with the gas storage chamber when the gas generating cartridge is mounted on the first cartridge mount, and, wherein gas is generated from the one or more gas generating materials in the gas generating cartridge and delivered to the gas storage chamber, wherein the first cartridge mount comprises a manifold that forms a gas flow path between the gas generating cartridge and the gas storage chamber;
        an inlet configured to receive gas delivered to the body cavity of the patient; and
        a second cartridge mount adapted to receive a gas harvesting cartridge, the gas harvesting cartridge configured to recycle at least one component of gas received at the inlet to the gas outlet and/or the gas storage chamber; and
        a gas control heater assembly positioned and configured to control a pressure of the gas delivered to the body cavity of the patient.

2. The insufflation apparatus of claim 1 wherein the gas generating cartridge is removable and further comprises at least one locking formation arranged to lock the gas generating cartridge on the first cartridge mount, wherein the at least one locking formation comprise a snap-fit formation or a spring clip.

3. The insufflation apparatus of claim 1 wherein the first cartridge mount comprises a cavity in the housing, the cavity being provided with an opening at an exterior of the housing, the gas generating cartridge being insertable through the opening and into the cavity in the housing.

4. The insufflation apparatus of claim 3 wherein the cavity is defined between at least two opposed walls, the gas generating cartridge being received between, and located against, the at least two opposed walls to fix an orientation of the gas generating cartridge relative to the first cartridge mount.

5. The insufflation apparatus of claim 1 wherein the manifold is intermediate the gas generating cartridge and the gas storage chamber when the gas generating cartridge is mounted on the first cartridge mount.

6. The insufflation apparatus of claim 1 wherein the first cartridge mount is arranged such that, with the gas generating cartridge mounted on the first cartridge mount, a direct fluid connection is formed between the gas generating cartridge and the gas storage chamber.

7. The insufflation apparatus of claim 1 comprising an isolator to isolate the gas storage chamber from the first cartridge mount such that the gas generating cartridge can be removed from the first cartridge mount without affecting the flow of gas from the gas storage chamber to the gas outlet.

8. The insufflation apparatus of claim 1, wherein the gas control heater assembly comprises a heater to control a reaction rate of the one or more gas generating materials and/or a temperature of the gas generated.

9. The insufflation apparatus of claim 1, wherein the gas control heater assembly comprises a chamber heater to heat gas inside the gas storage chamber.

10. The insufflation apparatus of claim 1 comprising a gas flow control valve provided between the gas storage chamber and the gas outlet to control the flow of gas through the gas outlet.

11. The insufflation apparatus of claim 10 wherein the gas flow control valve is controlled, automatically or manually, to vary at least one of a gas flow rate and the gas pressure.

12. The insufflation apparatus of claim 10 wherein the gas flow control valve additionally functions as a pressure relief valve to vent gas if a predetermined gas pressure is exceeded.

13. The insufflation apparatus of claim 1 comprising a passive mixing device provided in the gas flow path to generate turbulent flow in the gas to mix the gas.

14. The insufflation apparatus of claim 1 comprising a humidifier provided in the gas flow path to humidify the gas prior to the gas being delivered to the gas outlet.

15. The insufflation apparatus of claim 14 wherein the humidifier comprises an active humidifier comprising a liquid receptacle and a receptacle heater to heat liquid in the liquid receptacle.

16. The insufflation apparatus of claim 15 wherein the liquid receptacle is removably mounted on the housing such that the liquid receptacle can be removed and refilled or replaced.

17. The insufflation apparatus of claim 1 wherein any one or more of the following is provided in the gas flow path: a condenser, a heat exchanger, a flow enhancer, and an evaporator.

18. The insufflation apparatus of claim 1 comprising one or more additional inlets provided along the gas flow path to enable additives to be inserted into the gas flow.

19. The insufflation apparatus of claim 1 wherein a closure is provided at the gas generating cartridge and is arranged to seal the one or more gas generating materials in the gas generating cartridge, the insufflation apparatus being arranged to at least partially open the closure when the insufflation apparatus is in the active mode.

20. The insufflation apparatus of claim 1 wherein the gas control heater assembly is further configured to control a temperature of the gas delivered to the body cavity of the patient.

21. The insufflation apparatus of claim 1 wherein the gas control heater assembly is positioned in at least one of:
the housing;
between the first cartridge and the gas storage chamber; or
between the gas storage chamber and the gas outlet.

22. The insufflation apparatus of claim 1 wherein the gas control heater assembly is automatically controlled by a controller located within the insufflation apparatus.

23. The insufflation apparatus of claim 1 wherein the gas control heater assembly is controlled by a controller via operator input.

24. The insufflation apparatus of claim 1, wherein the gas control heater assembly comprises a first heater configured to control the pressure of the gas delivered to the body cavity of the patient.

25. The insufflation apparatus of claim 24, wherein the gas control heater assembly further comprises a second heater configured to control the temperature of the gas delivered to the body cavity of the patient.

26. The insufflation apparatus of claim 25, wherein the at least one of the first heater or the second heater comprise a chamber heater.

* * * * *